United States Patent
Mavromara et al.

(10) Patent No.: US 6,803,214 B1
(45) Date of Patent: Oct. 12, 2004

(54) NUCLEIC ACIDS AND NEW POLYPEPTIDES ASSOCIATED WITH AND/OR OVERLAPPING WITH HEPATITIS C VIRUS CORE GENE PRODUCTS

(75) Inventors: Penelope Mavromara, Athens (GR); Agoritsa Varaklioto, Athens (GR); Urania Georgopoulou, Athens (GR)

(73) Assignees: Institut Pasteur, Paris (FR); Hellenic Pasteur Institute, Athens (GR)

( * ) Notice: Subject to any disclaimer, the term of this patent is extended or adjusted under 35 U.S.C. 154(b) by 169 days.

(21) Appl. No.: 09/644,987

(22) Filed: Aug. 24, 2000

Related U.S. Application Data

(60) Provisional application No. 60/151,074, filed on Aug. 27, 1999.

(51) Int. Cl.[7] ................................................. C12P 21/02
(52) U.S. Cl. ................ 435/69.3; 435/235.1; 435/320.1; 435/252.33; 435/325; 435/254.11; 435/254.21
(58) Field of Search ........................... 435/235.1, 320.1, 435/69.3, 6, 252.33, 325, 254.11, 254.21

(56) References Cited

U.S. PATENT DOCUMENTS 5,625,034 A * 4/1997 Liao et al. .................. 530/350

* cited by examiner

*Primary Examiner*—James Ketter
(74) *Attorney, Agent, or Firm*—Finnegan Henderson Farabow Garrett & Dunner, L.L.P.

(57) ABSTRACT

DNA encoding core+1 polypeptides of hepatitis C virus (HCV), nucleotides encoding the polypeptides, and methods for using the nucleotides and the encoded polypeptides are disclosed.

13 Claims, 26 Drawing Sheets

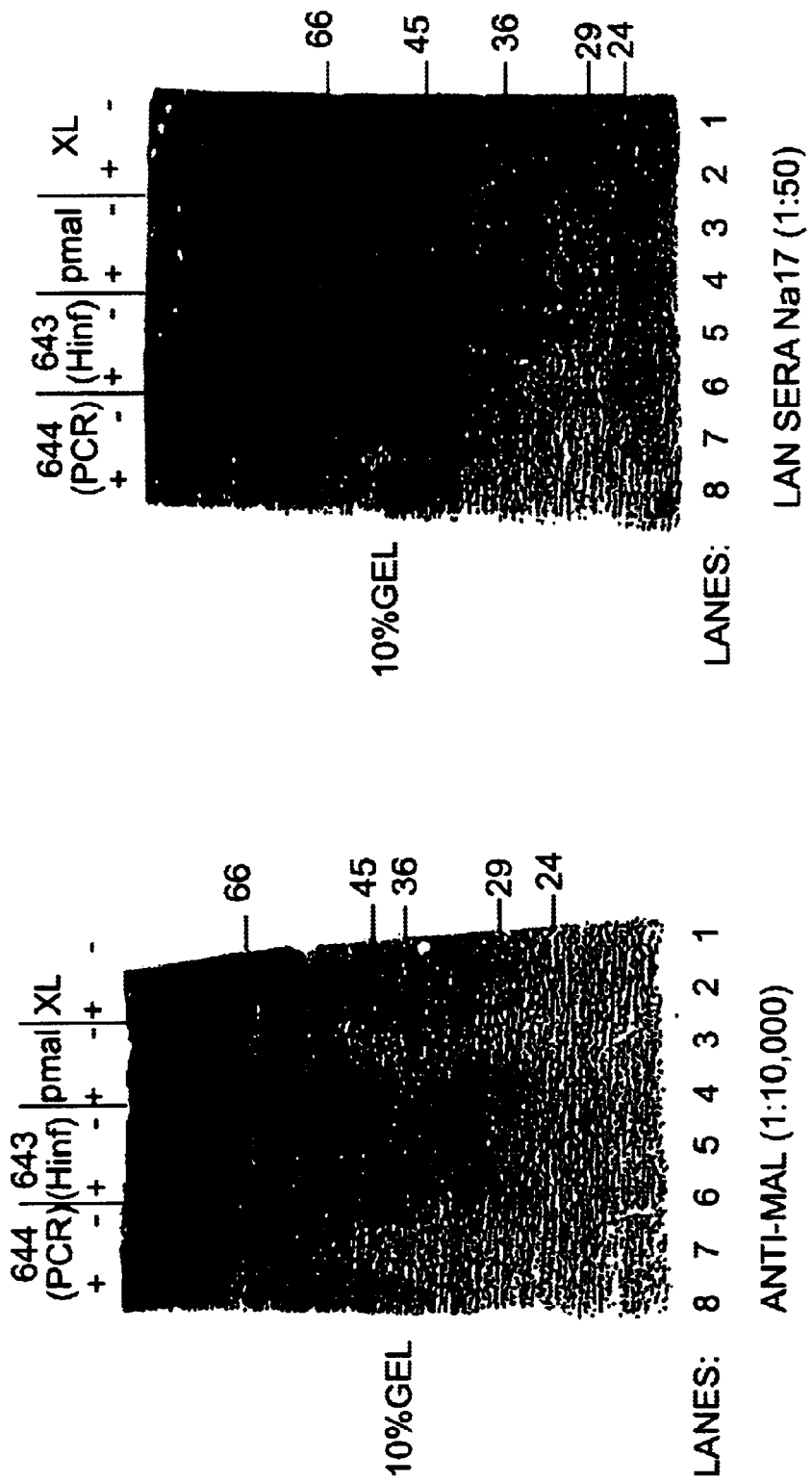

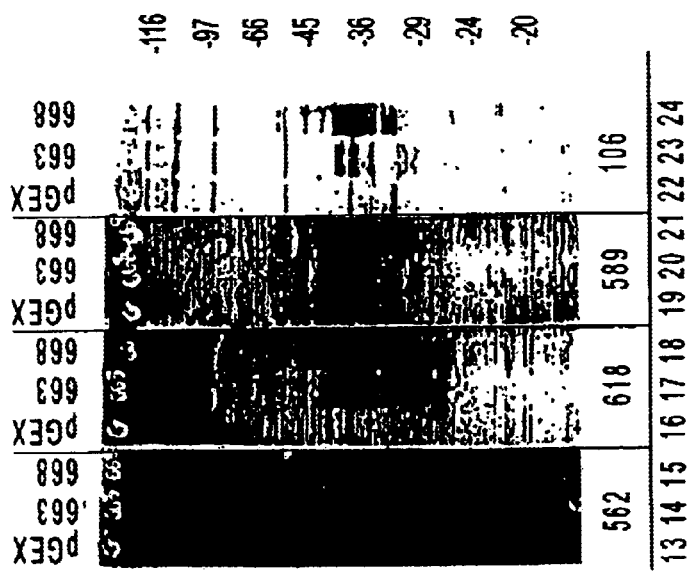
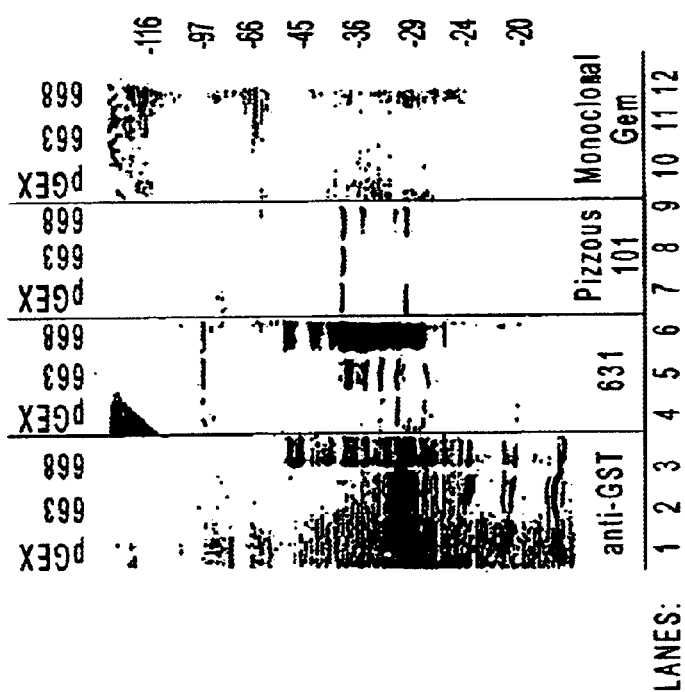
FIG. 6

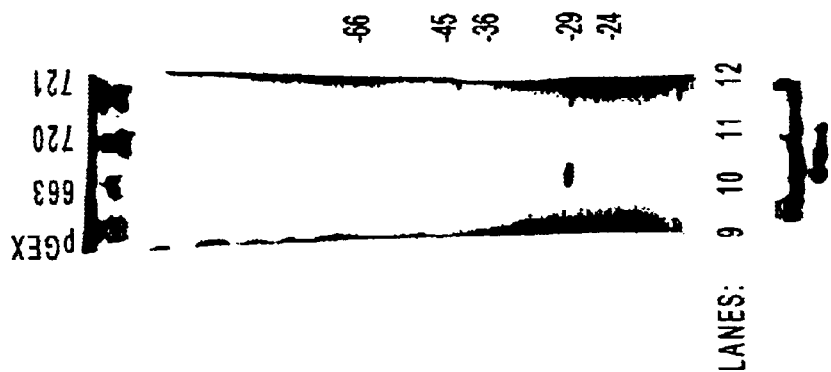
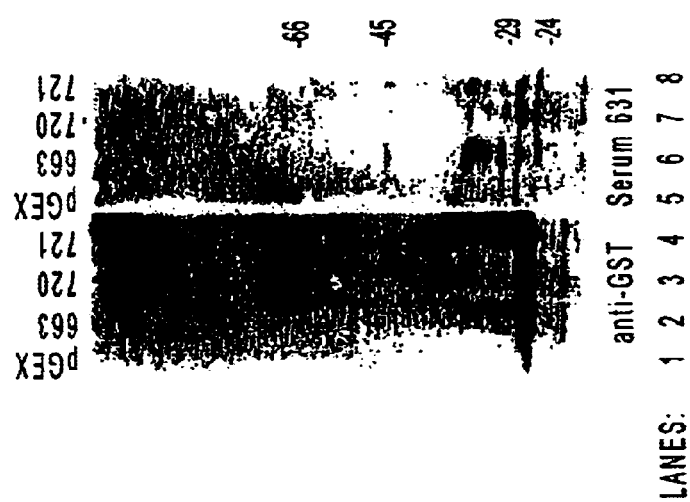
FIG. 8

WILD TYPE
pHPI 643 & pHPI 663

(SEQ ID NO: 11)

(SEQ ID NO: 12)

(SEQ ID NO: 13)

(SEQ ID NO: 14)

(SEQ ID NO: 15)

SEQUENCE RANGE: 342 TO 840

```
              350           360           370           380           390
               *             *             *             *             *
(SEQ ID NO:2) A TGA GCA CGA ATC CTA AAC CTC AAA AAA ACA AAC GTA ACA CCA ACC
(SEQ ID NO:1) T ACT CGT GCT TAG GAT TTG GAG TTT TGT TTG CAT TGT GGT TGG
             *** Ala Arg Ile Leu Asn Leu Lys Lys Thr Asn Val Thr Pro Thr>
              ___a_____a_____>
                    TRANSLATION OF HCVSEND.SEQ (RITSA) [A]

400           410           420           430
               *             *             *             *
              GTC GCC CAC AGG ACG TCA AGT TCC CGG GTG GCG GTC AGA TCG TTG GTG
              CAG CGG GTG TCC TGC AGT TCA AGG GCC CAC CGC CAG TCT AGC AAC CAC
              Val Ala His Arg Thr Ser Ser Arg Val Ala Val Arg Ser Leu Val>
              ___a_____a_____>
                    TRANSLATION OF HCVSEND.SEQ (RITSA) [A]
                         PUTATIVE
                      SLIPPERY SIGNAL 440           450           460           470           480
               *             *             *             *             *
              GAG TTT ACT TGT TGC CGC GCA GGG GCC CTA GGC GCA GAT TGG GTG TGC GCG CGA
              CTC AAA TGA ACA ACG GCG CGT CCC CGG GAT CCG CGT CTA ACC CAC ACG CGC GCT
              Glu Phe Thr Cys Cys Arg Ala Gly Ala Leu Asp Trp Val Cys Ala Arg>
              ___a_____a_____>
                    TRANSLATION OF HCVSEND.SEQ (RITSA) [A]
```

FIG. 12A

```
        490           500           510           520           530
         *             *             *             *             *
CGA GAA AGA CTT CCG AGC GGT CGC AAC CTC GAG GTA GAC GTC CAG TCG AGC CTA
GCT CTT TCT GAA GGC TCG CCA GCG TTG GAG CTC CAT CTG CAG TCG GAT
Arg Glu Arg Leu Pro Ser Gly Arg Asn Leu Glu Val Asp Val Ser Leu>
    a             a             a             a             a
                  TRANSLATION OF HCVSEND.SEQ (RITSA) [A]

540           550           560           570           580
         *             *             *             *             *
TCC CCA AGG CTC GTC GGC CCG AGG GCA GGA CCT GGG CTC AGC CCG GGT
AGG GGT TCC GAG CAG CCG GGC TCC CGT CCT GGA CCC GAG TCG GGC CCA
Ser Pro Arg Leu Val Gly Pro Arg Ala Gly Pro Gly Leu Ser Pro Gly>
    a             a             a             a             a
                  TRANSLATION OF HCVSEND.SEQ (RITSA) [A]

590           600           610           620           630
         *             *             *             *             *
ACC CTT GGC CCC TCT ATG GCA ATG AGG GCT GCG GGT GGG CGG GAT GGC
TGG GAA CCG GGG AGA TAC CGT TAC TCC CGA CGC CCA CCC GCC CTA CCG
Thr Leu Gly Pro Ser Met Ala Met Arg Ala Ala Gly Gly Arg Asp Gly>
    a             a             a             a             a
                  TRANSLATION OF HCVSEND.SEQ (RITSA) [A]
```

*FIG. 12B*

```
                640              650              660              670
                 *                *                *                *
TCC TGT CTC CCC GTG GCT CTC GGC CTA GCT GGG GCC CCA CAG ACC CCC
AGG ACA GAG GGG CAC CGA GAG CGG GAT CGA CCG GGT GTC TGG GGG
Ser Cys Leu Pro Val Ala Leu Gly Leu Ala Gly Ala Pro Gln Thr Pro>
 a____a____a____a____TRANSLATION OF HCVSEND.SEQ (RITSA) [A] a____a____a____>

680              690              700              710              720
                 *                *                *                *                *
GGC GTA GGT CGC GCA ATT TGG GTA AGG TCA CAT TCC AGT AGC TAT GGG AAT GCA CGC
CCG CAT CCA GCG CGT TAA ACC CAT TCC AGT GTA AGG TCA ATA CCC TTA CGT GCG
Gly Val Gly Arg Ala Ile Trp Val Arg Ser His Ser Ser Ile Pro Leu Arg Ala>
 a____a____a____a____TRANSLATION OF HCVSEND.SEQ (RITSA) [A] a____a____a____>

730              740              750              760              770
                 *                *                *                *                *
GCT TCG CCG ACC TCA GGT ACA TAC CGC TCG GCG CCC CTC TTG
CGA AGC GGC TGG AGT ACC ATG GGT ACG TGT ATG AGC AGC GCG CGG GAG AAC
Ala Ser Pro Thr Ser Trp Gly Thr Tyr Arg Ser Ser Ala Pro Leu Leu>
 a____a____a____a____TRANSLATION OF HCVSEND.SEQ (RITSA) [A] a____a____a____>
```

*FIG. 12C*

```
                                    780                 790                 800                 810                 820
                                     *                   *                   *                   *                   *
                                 GAG GCG CTG CCA GGG CCC TGG CGC ATG GCG TCC GGG TTC TGG AAG ACG
                                 CTC CGC GAC GGT CCC GGG ACC GCG TAC CGC AGG CCC AAG ACC TTC TGC
                                 Glu Ala Leu Pro Gly Pro Trp Arg Met Ala Ser Gly Phe Trp Lys Thr>
                                  *    a    a   TRANSLATION OF HCVSEND.SEQ (RITSA) [A]  a    a    a    >

830                 840
                                     *                   *
                                 GCG TGA ACT ATG CAA CAG
                                 CGC ACT TGA TAC GTT GTC
                                 Ala *** Thr Met Gln Gln>
                                  *  TRANSLATION OF H         >
```

*FIG. 12D*

SEQUEBCE RANGE: 1 TO 166

```
         10         20         30         40         50         60
          *          *          *          *          *          *
*ARILNLKKK TNVTPTVAHR TSSSRVAVRS LVEFTCCRAG ALDWVCARRE RLPSGRNLEV 70         80         90        100        110        120
          *          *          *          *          *          *
DVSLSPRLVG PRAGPGLSPG TLGPSMAMRA AGGRDGSCLP VALGLAGAPQ TPGVGRAIWV 130        140        150        160
          *          *          *          *
RSSIPLRAAS PTSWGTYRSS APLLEALPGP WRMASGFWKT A*TMQQ
```

FIG. 13

(SEQ ID NO:1)

NUCLEIC ACIDS AND NEW POLYPEPTIDES ASSOCIATED WITH AND/OR OVERLAPPING WITH HEPATITIS C VIRUS CORE GENE PRODUCTS

CROSS-REFERENCE TO RELATED APPLICATIONS

This application hereby claims the benefit under 35 U.S.C. §119(e) of United States provisional application Ser. No. 60/151,074 filed Aug. 27, 1999. The entire disclosure of this application is relied upon and incorporated by reference herein.

FIELD OF THE INVENTION

The invention is directed to purified and isolated polypeptides, the nucleic acids encoding such polypeptides, processes for production of recombinant forms of such polypeptides, antibodies generated against these polypeptides, and the use of such nucleic acids and polypeptides in diagnostic methods, kits, vaccines, or antiviral therapy.

BACKGROUND OF THE INVENTION

Hepatitis C virus (HCV) is an important etiologic agent of hepatocellular carcinoma (HCC). However, the mechanism of carcinogenesis by HCV is poorly understood. Although liver cirrhosis caused by the virus may be of primary importance in triggering the malignant transformation of hepatocytes, recent evidence suggested that some HCV proteins have transforming capacities and thus can be implicated in the pathogenesis of HCC (Ray et al., 1996; Sakamuro et al., 1995).

The HCV genome is a plus-stranded RNA about 10 kb in length that encodes a single polyprotein of 3009–3010 amino acids processed co- or post-translationally by both cellular and viral proteinases to produce at least 10 mature structural and non-structural viral proteins. The structural proteins are located in the amino terminal quarter of the polyprotein, and the non-structural (NS) polypeptides in the remainder (for a review see Houghton, 1996). The genome organization resembles that of flavi- and pestiviruses, and HCV is now considered to be a member of the Flaviviraidae family (Miller and Purcell, 1990; Ohba et al., 1996).

The gene products of HCV are, from the N-terminus to the C-terminus: core (p22), E1 (gp35), E2 (gp 70), NS2 (p21), NS3 (p70), NS4a(p4), NS4b (p27), NS5a (p58), NS5b (p66). Core, E1, and E2 are the structural proteins of the virus processed by the host signal peptidase(s). The core protein and the genomic RNA constitute the internal viral core and E1 and E2 together with lipid membrane constitute the viral envelope (Dubuisson et al., 1994; Grakoui et al., 1993; Hijikata et al., 1993). The NS proteins are processed by the viral protein NS3, which has two functional domains: one (Cpro-1), encompassing the NS2 region and the N-terminal portion of NS3, which cleaves autodatalytically between NS2 and NS3, and the other (Cpro-2), located solely in the N-terminal portion of NS3, cleaves the other sites downstream NS3 (Bartenschalger et al., 1995; Hijikata et al., 1993).

One of the characteristics of HCV is its high degree of genetic heterogeneity in vivo, manifested both in the generation of viral quasi-species and in the continuous emergence of neutralization escape mutants (Shimizu et alk., 1994). This poses an obstacle to the development of a broadly reactive HCV vaccine based on antibody reactivity to the envelope glycoproteins (Chien et al., 1993).

Although alpha interferon has been shown to be useful for delaying the development of HCC in chronically infected HCV patients (Nishiguchi et al., 1995), a highly effective therapeutic agent has not yet been developed to control this important infection and to prevent HCC development. For these reasons, there is a considerable need for the development of a detailed understanding of HCV proteins, which should clarify the mechanisms by which HCV induces hepatocyte transformation. Such an understanding may lead to effective means to treat or control the infection, as well as aid in the diagnosis of HCV infection in humans.

SUMMARY OF THE INVENTION

Accordingly, this invention aids in fulfilling these needs in the art. The invention encompasses a purified nucleic acid molecule comprising the DNA sequence of SEQ ID NO:2 and a purified nucleic acid molecule encoding the amino acid sequence of SEQ ID NO:1. The invention also encompasses nucleic acid molecules complementary to these sequences.

The invention also encompasses purified polypeptides encoded by these nucleic acid molecules, including purified polypeptides having a molecular weight of approximately 17.5 kD, as predicted by the sequence, hybrid proteins containing amino acid sequences from core and core+1, and purified polypeptides in non-glycosylated form.

The invention includes double-stranded nucleic acid molecules comprising the DNA sequence of SEQ ID NO:2 and purified nucleic acid molecules encoding the amino acid sequence of SEQ ID NO:1. Both single-stranded and double-stranded RNA and DNA nucleic acid molecules are encompassed by the invention. These molecules can be used to detect both single-stranded and double-stranded RNA and DNA variants of encoding polypeptides encompassed by the invention. A double-stranded DNA probe allows the detection of nucleic acid molecules equivalent to either strand of the nucleic acid molecule.

Purified nucleic acid molecules that hybridize to a denatured, double-stranded DNA comprising the DNA sequence of SEQ ID NO:2 or an purified nucleic acid molecule encoding the amino acid sequence of SEQ ID NO:1 under conditions of moderate stringency in 50% formamide and 6×SSC, at 42° C. with washing conditions of 60° C., 0.5×SSC, 0.1% SDS are encompassed by the invention.

The invention further encompasses purified nucleic acid molecules derived by in vitro mutagenesis from SEQ ID NO:2. In vitro mutagenesis includes numerous techniques known in the art including, but not limited to, site-directed mutagenesis, random mutagenesis, and in vitro nucleic acid synthesis.

The nucleic acid molecules of the invention, which include DNA and RNA, are referred to herein as "core+1 nucleic acids" or "core+1 DNA", and the amino acids encoded by these molecules are referred to herein as "core+1 polypeptides."

The invention also encompasses purified nucleic acid molecules degenerate from SEQ ID NO:2 as a result of the genetic code, purified nucleic acid molecules, which are allelic variants of core+1 nucleic acids or a species homolog of core+1 nucleic acids. The invention also encompasses recombinant vectors that direct the expression of these nucleic acid molecules and host cells transformed or transfected with these vectors.

Purified polyclonal or monoclonal antibodies that bind to core+1 polypeptides are encompassed by the invention.

The invention further encompasses methods for the production of core+1 polypeptides, including culturing a host cell under conditions promoting expression, and recovering the polypeptide from the culture medium. Especially, the expression of core+1 polypeptides in bacteria, yeast, plant, and animal cells is encompassed by the invention.

This invention also provides labeled core+1 polypeptides. Preferably, the labeled polypeptides are in purified form. It is also preferred that the unlabeled or labeled polypeptide is capable of being immunologically recognized by human body fluid containing antibodies to HCV. The polypeptides can be labeled, for example, with an immunoassay label selected from the group consisting of radioactive, enzymatic, fluorescent, chemiluminescent labels, and chromophores.

Immunological complexes between the core+1 polypeptides of the invention and antibodies recognizing the polypeptides are also provided. The immunological complexes can be labeled with an immunoassay label selected from the group consisting of radioactive, enzymatic, fluorescent, chemiluminescent labels, and chromophores.

Furthermore, this invention provides a method for detecting infection by HCV. The method comprises providing a composition comprising a biological material suspected of being infected with HCV, and assaying for the presence of core+1 polypeptide of HCV. The polypeptides are typically assayed by electrophoresis or by immunoassay with antibodies that are immunologically reactive with core+1 polypeptides of the invention.

This invention also provides an in vitro diagnostic method for the detection of the presence or absence of antibodies, which bind to an antigen comprising the core+1 polypeptides of the invention or mixtures of the polypeptides. The method comprises contacting the antigen with a biological fluid for a time and under conditions sufficient for the antigen and antibodies in the biological fluid to form an antigen-antibody complex, and then detecting the formation of the complex. The detecting step can further comprising measuring the formation of the antigen-antibody complex. The formation of the antigen-antibody complex is preferably measured by immunoassay based on Western blot technique, ELISA (enzyme linked immunosorbent assay), indirect immunofluorescent assay, or immunoprecipitation assay.

A diagnostic kit for the detection of the presence or absence of antibodies, which bind to the core+1 polypeptide of the invention or mixtures of the polypeptides, contains antigen comprising the core+1 polypeptide, or mixtures thereof, and means for detecting the formation of immune complex between the antigen and antibodies. The antigens and the means are present in an amount sufficient to perform the detection.

This invention also provides an immunogenic composition comprising a core+1 polypeptide of the invention or a mixture thereof in an amount sufficient to induce an immunogenic or protective response in vivo, in association with a pharmaceutically acceptable carrier therefor. A vaccine composition of the invention comprises a neutralizing amount of the core+1 polypeptide and a pharmaceutically acceptable carrier therefor.

The polypeptides of this invention are thus useful as a portion of a diagnostic composition for detecting the presence of antibodies to antigenic proteins associated with HCV.

In addition, the core+1 polypeptides can be used to raise antibodies for detecting the presence of antigenic proteins associated with HCV.

The polypeptides of the invention can be also employed to raise neutralizing antibodies that either inactivate the virus, reduce the viability of the virus in vivo, or inhibit or prevent viral replication. The ability to elicit virus-neutralizing antibodies is especially important when the proteins and polypeptides of the invention are used in immunizing or vaccinating compositions to activate the B-cell arm of the immune response or induce a cytotoxic T lymphocyte response (CTL) in the recipient host.

Finally, this invention provides a method for detecting the presence or absence of hepatitis C virus (HCV) comprising:

(1) contacting a sample suspected of containing viral genetic material of HCV with at least one nucleotide probe, and (2) detecting hybridization between the nucleotide probe and the viral genetic material in the sample, wherein said nucleotide probe is complementary to the full-length sequence of the purified core+1 nucleic acids of the invention.

BRIEF DESCRIPTION OF THE DRAWINGS

This invention will be more fully described with reference to the drawings in which:

FIG. 2 is a Western blot analysis of cell lysates using polyclonal anti-mal antiserum. Panel A, Lanes 1 and 2, represent XL-1 blue bacteria harboring no plasmid, lanes 3 and 4 represent bacteria harboring pmal-c2 vector, lanes 5 and 6 represent bacteria harboring plasmid pHPI 643, and lanes 7 and 8 represent bacteria harboring plasmid pHPI 644.

Panel B of FIG. 2 is a Western blot analysis of cell lysates using HCV positive human serum. Lanes 1 and 2 represent XL-1 blue bacteria harboring no plasmid, lanes 3 and 4 represent bacteria harboring pmal-c2 vector, lanes 5 and 6 represent bacteria harboring plasmid pHPI 643, and lanes 7 and 8 represent bacteria harboring plasmid pHPI 644. Odd numbers correspond to bacteria, which were not induced, and even numbers correspond to bacteria inducted with 0.5 mM IPTG.

Figure 3A:
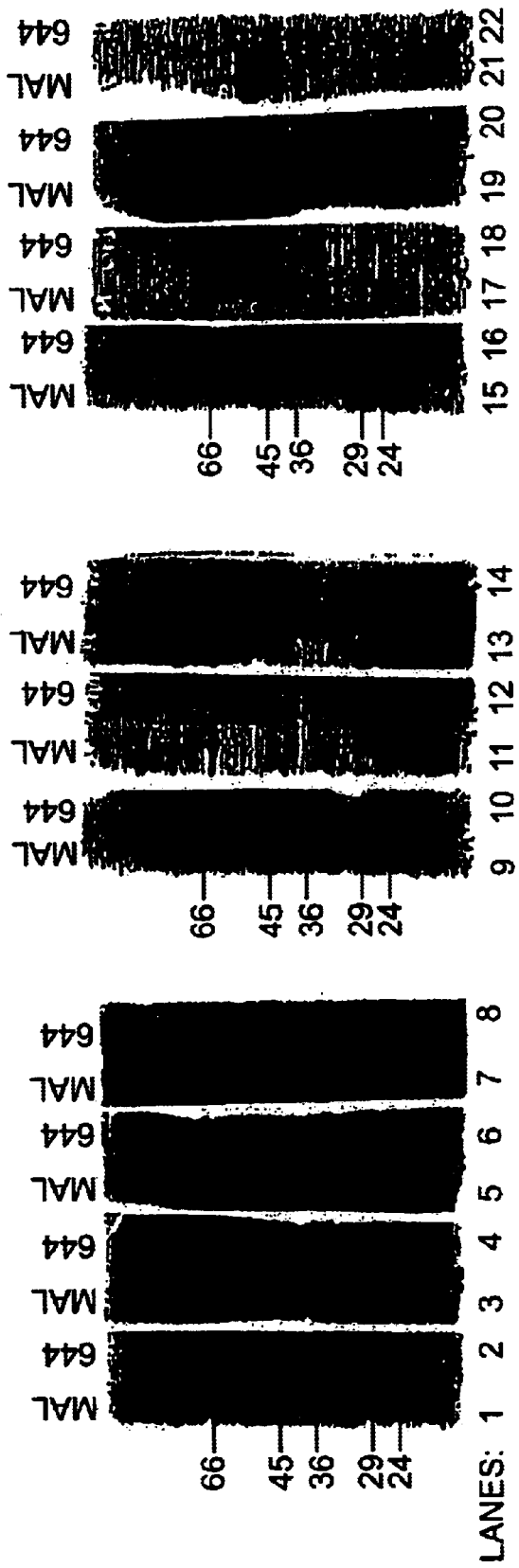
Figure 3B:
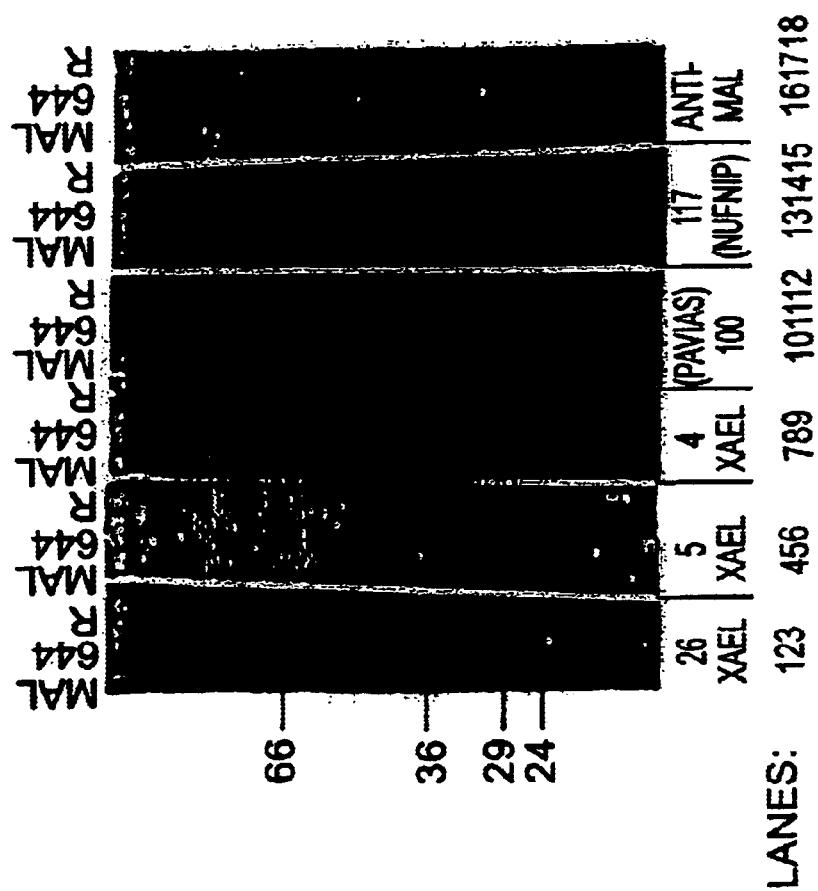

FIG. 3 is a Western blot analysis of cell lysates using a panel of previously characterized HCV positive human sera. Panel A, Lanes 1, 3, 5, 7, 9, 11, 13, 15, 17, and 19 represent XL-1 blue bacteria harboring pmal-c2 vector. Lanes 2, 4, 6, 8, 10, 12, 14, 16, 18, and 20 represent bacteria harboring plasmid pHPI 644 (expressing the truncated core+1 protein). Lanes 21 and 22 represent bacteria harboring pmal-c2 vector and plasmid pHPI 644, respectively, which were tested against polyclonal anti-mal antiserum.

Panel B of FIG. 3 is a Western blot analysis of cell lysates using a panel of previously characterized HCV positive and negative human sera. Lanes 1, 4, 7, 10, 13, and 16 represent XL-1 blue bacteria harboring pmal-c2 vector. Lanes 2, 5, 8, 11, 14, and 17 represent bacteria harboring plasmid pHPI 644 (expressing the truncated core+1 protein). Serum numbers 5 and 4 correspond to HCV positive human sera; serum numbers 26, 100, and 117 correspond to HCV negative human sera.

Figure 4A:
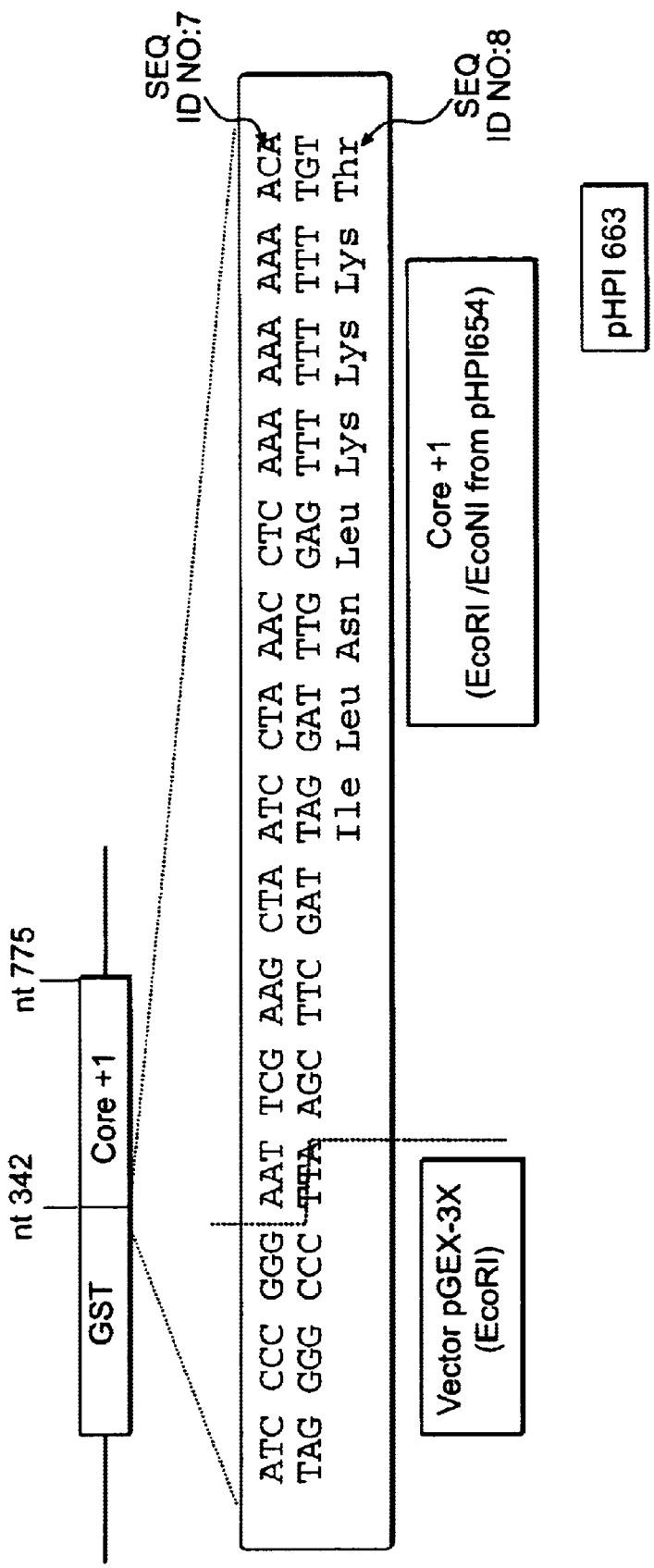
Figure 4B:
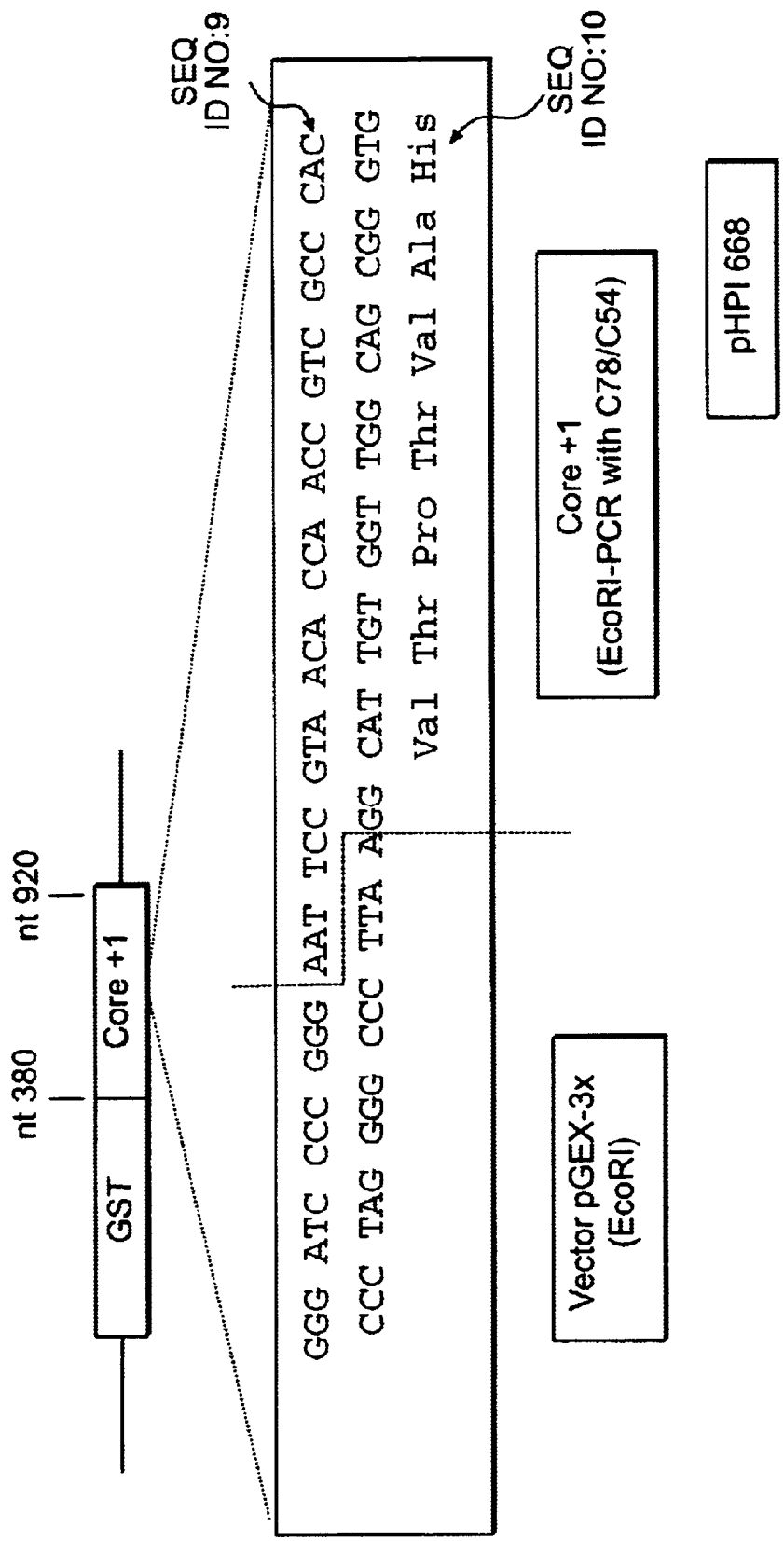

FIG. 4 describes two plasmids of the invention, pHPI 663 (SEQ ID NOS: 7 and 8) and pHPI 668 (SEQ ID NOS: 9 and 10).

Figure 5:
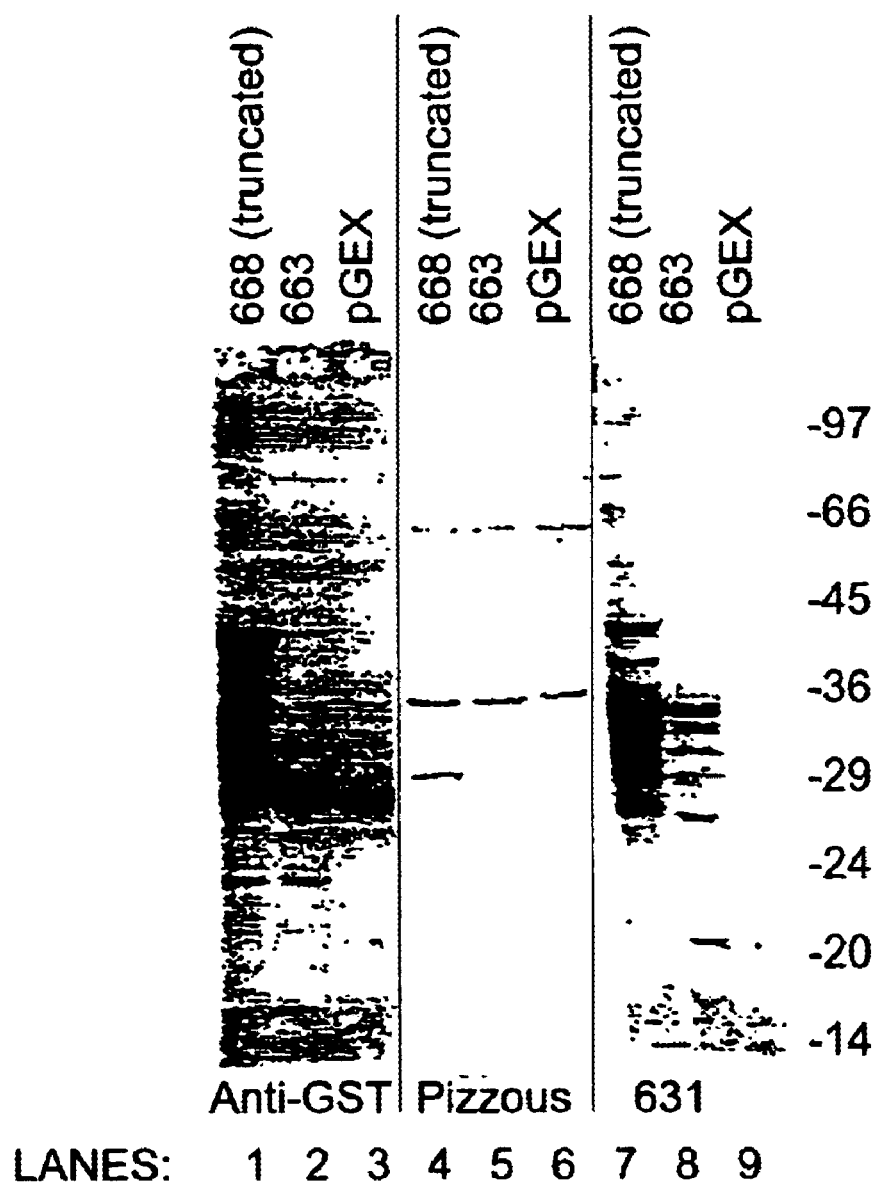

FIG. 5 is a Western blot analysis of cell lysates using polyclonal anti-GST antiserum (lanes 1, 2, and 3), HCV negative human serum (lanes 4, 5 and 6), and HCV positive human serum (lanes 7, 8, and 9). Lanes 3, 6, and 9 correspond to bacteria harboring the pGEX-3x vector, lanes 2, 5, and 8 correspond to bacteria harboring plasmid pHPI 663 (large part of core+1 DNA), and lanes 1, 4 and 7 correspond to bacteria harboring plasmid pHPI 668 (truncated part of core+1 DNA).

FIG. 6 is a Western blot analysis of cell lysates using a panel of previously characterized HCV positive and negative human sera. Lanes 1, 4, 7, 10, 13, 16, 19, and 22 represent XL-1 blue bacteria harboring pGEX-3x vector. Lanes 2, 5, 8, 11, 14, 17, 20, and 23 represent bacteria harboring plasmid pHPI 663 (expressing the large part of core+1 protein). Lanes 3, 6, 9, 12, 15, 18, 21, and 24 represent bacteria harboring plasmid pHPI 668 (expressing the truncated part of core+1 protein). Serum numbers 631, 562, 618, 589, and 106 correspond to HCV-positive human sera. Serum number 101 corresponds to HCV-negative human serum.

Figure 7A:
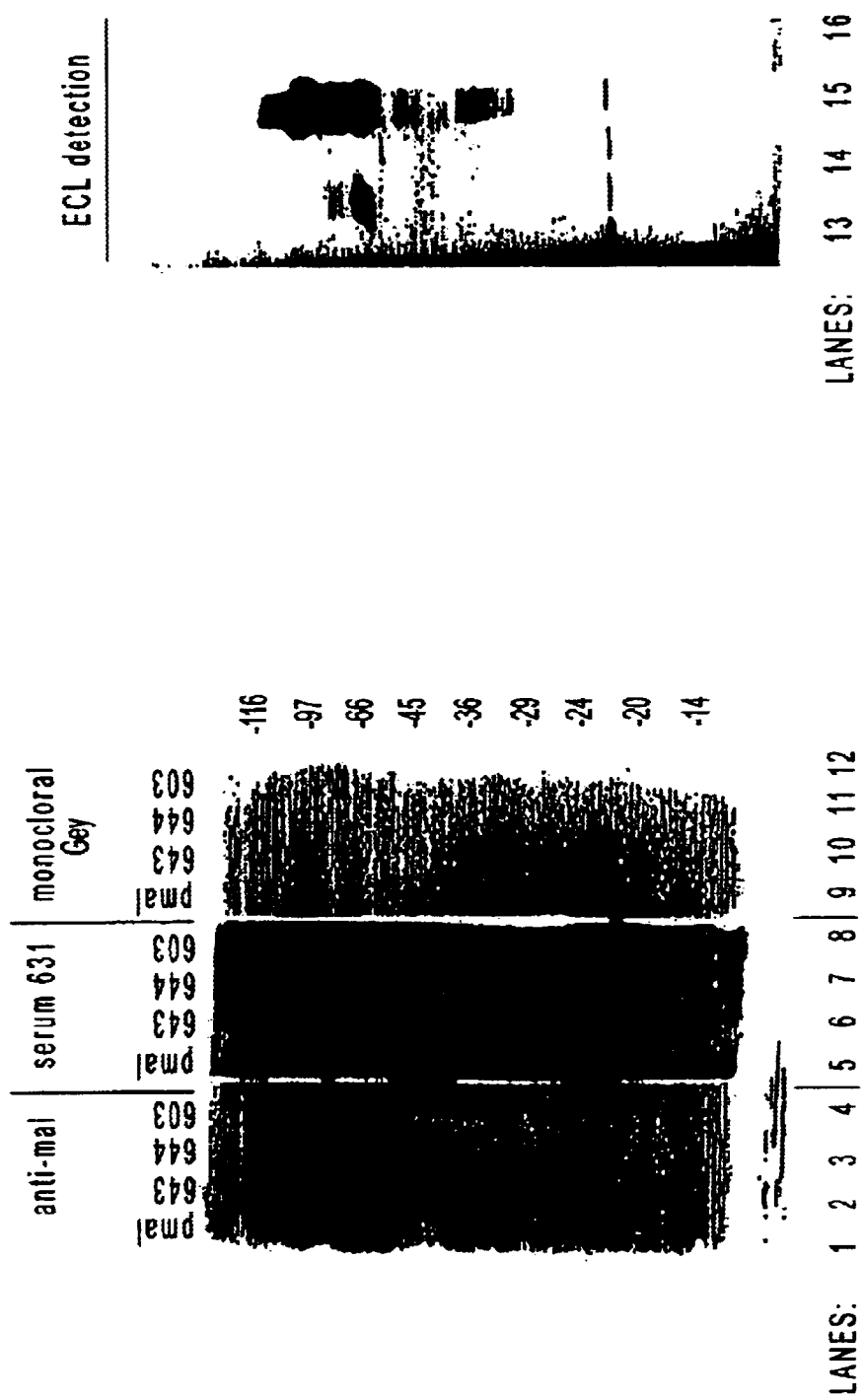
Figure 7B:
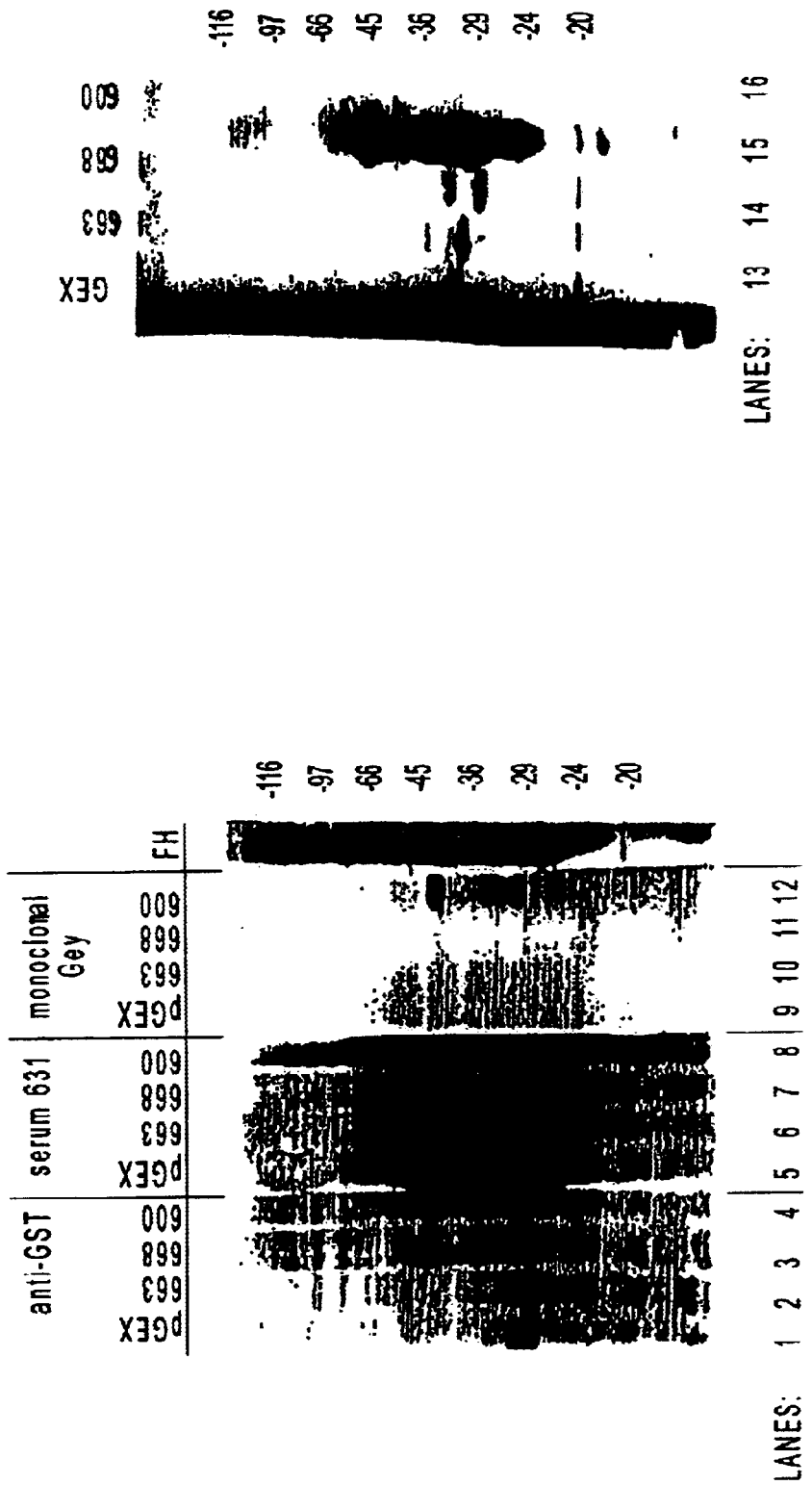

FIG. 7, Panel A is a Western blot analysis of cell lysates using polyclonal anti-mal antiserum (lanes 1, 2, 3, and 4), HCV-positive human serum (lanes 5, 6, 7, and 8) and monoclonal antibody against core protein (lanes 9, 10, 11, and 12). Lanes 13–16, are the same as lanes 9–12, but detected with the ECL chemiluminescence method. Lanes 1, 5, 9, and 13 correspond to bacteria harboring pmal-c2 vector. Lanes 2, 6, 10, and 14 correspond to bacteria harboring plasmid pHPI 643 (large part of core+1 protein). Lanes 3, 7, 11, and 15 correspond to bacteria harboring plasmid pHPI 644 (truncated core+1 protein). Lanes 4, 8, 12, and 16 correspond to bacteria harboring plasmid pHPI 603 (expressing malE-core fusion protein).

Panel B is a Western blot analysis of cell lysates using polyclonal anti-GST antiserum (lanes 1, 2, 3, and 4), HCV-positive human serum (lanes 5, 6, 7, and 8), and monoclonal antibody against core protein (lanes 9, 10, 11, and 12 colorimetric detection). Lanes 13, 14, 15, and 16 are similar to lanes,9–12, but detected with chemiluminescence ECL detection). Lanes 1, 5, 9, and 13 correspond to bacteria harboring pGEX-3x vector. Lanes 2, 6, 10, and 14 correspond to bacteria harboring plasmid pHPI 663 (large part of core+1 protein). Lanes 3, 7, 11, and 15 correspond to bacteria harboring plasmid pHPI 668 (truncated core+1 protein). Lanes 4, 8, 12, and 16 correspond to bacteria harboring plasmid pHPI 600 (expressing GST-core fusion protein).

FIG. 8 is a Western blot analysis of cell lysates using polyclonal anti-GST antiserum (lanes 1, 2, 3, and 4), HCV-positive human serum (lanes 5, 6, 7, and 8) detected with the calorimetric ($H_2O_2$) method. Western blot analysis of cell lysates using monoclonal antibody against core protein (lanes 9, 10, 11, and 12) detected with the ECL chemiluminescence method.

Lanes 1, 5, and 9 correspond to bacteria harboring pGEX-3X vector.

Lanes 2, 6, and 10 correspond to bacteria harboring plasmid pHPI 663 (GST-core+1-L protein).

Lanes 3, 7, and 11 correspond to bacteria harboring plasmid pHPI 720 (GST-core+1-L protein; mutation R4).

Lanes 4, 8, and 12 correspond to bacteria harboring plasmid pHPI 721 (GST-core+1-L protein; mutation R5).

Figure 9B:
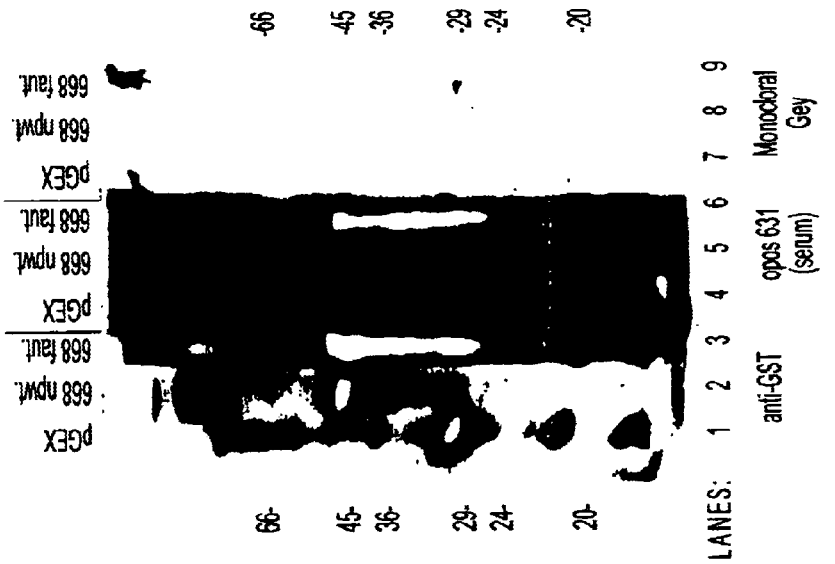
Figure 9A:
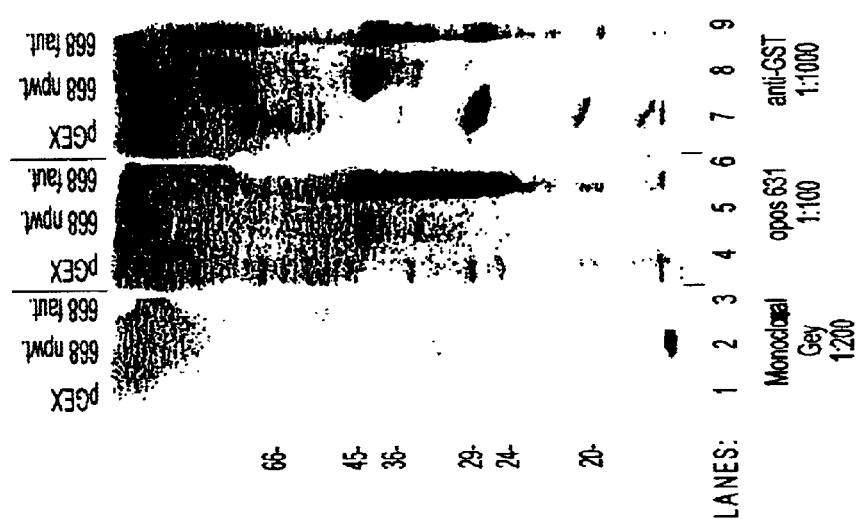
Figure 9C:

FIG. 9, Panel A is a Western blot analysis of cell lysates and purified GST-core+1 proteins using monoclonal antibody against core protein antiserum (lanes 1, 2, and 3), HCV-positive human serum (lanes 4, 5, and 6) and polyclonal anti-GST (lanes 7, 8, and 9). The calorimetric ($H_2O_2$) detection was used.

Panel B is exactly the same blot as Panel A, but the ECL chemiluminescence detection was used. Western blot using polyclonal anti-GST antiserum (lanes 1, 2, and 3), HCV-positive human serum (lanes 4, 5, and 6), and monoclonal antibody against core protein (lanes 7, 8, and 9).

Lanes 1, 4, and 7 correspond to bacteria harboring plasmid pHPI 668.

Lanes 2, 5, and 8 correspond to the purified GST-core+1 protein (purified by electroelution).

Lanes 3, 6, and 9 correspond to bacteria harboring plasmid pHPI 668.

Panel C is a coomassie stained SDS-gel of cell lysates and purified GST-core+1 protein.

Lane 1 corresponds to the molecular weight marker.

Lane 2 corresponds to bacteria harboring plasmid pHPI 668.

Lane 3 corresponds to the purified GST-core+1 protein (purified by electroelution).

Lane 4 corresponds to bacteria harboring pGEX-3X vector.

FIGS. 10 (a–f). Potential RNA structures of the wild type and mutated 5' terminus of the HCV RNA (nt1-480) as predicted by the mfold program. The sequence shown is the consensus sequence for HCV type 1a. The nucleotides of the initiator AUG codon are boxed. Arrows indicate the changes derived from the mutatgenesis experiments. FIG. 10a (SEQ ID NO: 11) wild type sequences present in pHPI643 and pHPI663; FIG. 10b (SEQ ID NO: 12), substitution present in pHPI676; FIG. 10c (SEQ ID NO: 13), substitutions present in pHPI679; FIG. 10d (SEQ ID NO: 14), substitutions present in pHPI1719; FIG. 10e (SEQ ID NO: 15) substitutions present in pHPI720; FIG. 10f (SEQ ID NO: 16) substitution present in pHPI721.

Figure 11:
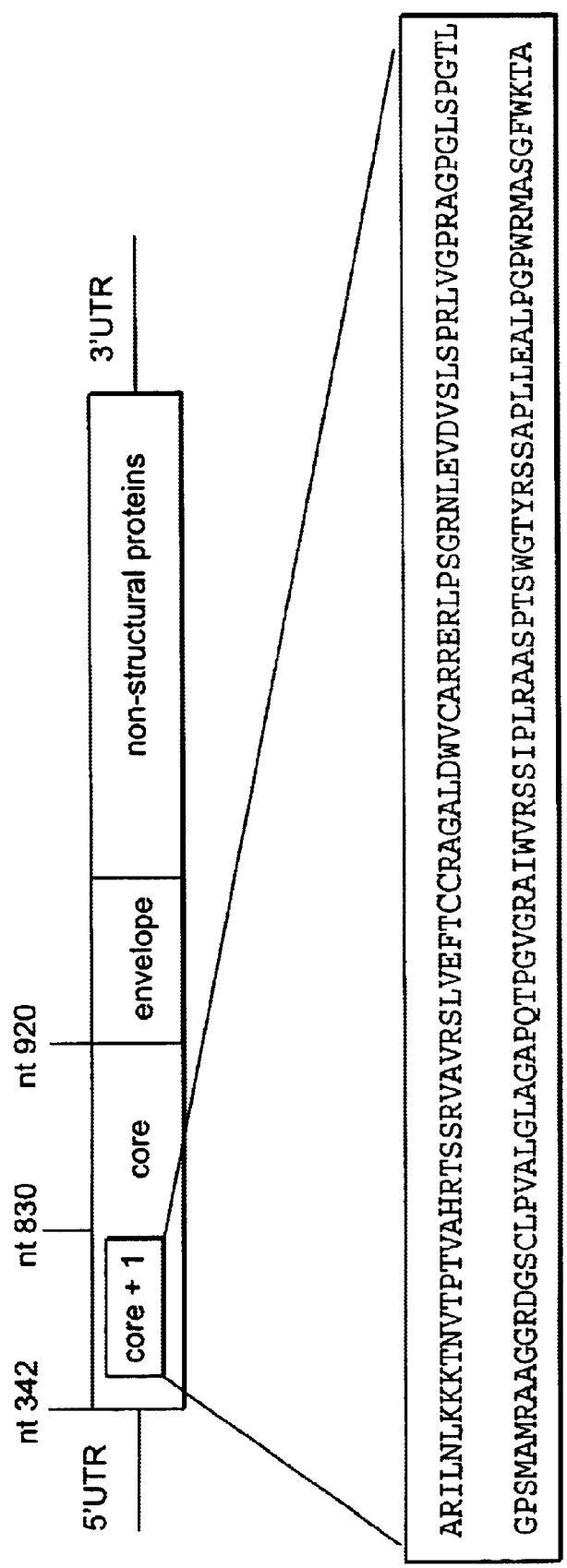

FIG. 11 shows the sequence of a polypeptide of the invention in standard single letter abbreviations (amino acids 1 to 161 of SEQ ID NO: 1) designated herein as "core+1 protein", and its relationship to the core gene of HCV. The amino acids in bold type designate amino acids present in the catalytic site of the papain-like proteases.

FIG. 12 contains the nucleotide sequence of core+1 DNA (SEQ ID NO: 2) and the amino acid sequence of core+1 protein (SEQ ID NO: 1). Specifically, the first line in FIG. 12 is the nucleotide sequence of the coding strand, second line is the nucleotide sequence of the complementary strand, the third line is the amino acid sequence of the novel polypeptide, and the fourth line is produced by the computer program (McVector). A putative "slippery site(s)" and/or novel RNA signal(s) is identified between nucleotides 345 and 460.

FIG. 13 contains the sequence of core+1 protein (SEQ ID NO:1) of the invention.

DETAILED DESCRIPTION OF THE INVENTION

An HCV RNA sequence has been discovered, which synthesizes a novel polypeptide that is contained within nt 342–830 and is the product of a +1 frame probably by shifting at a "slippery site" inside the core region. A UGA stop codon is within the $162^{nd}$ codon of the core gene in HCV-1a strain. Thus, the novel polypeptide is expected to have approximately 160 amino acid residues and MW ~17.5 kDa. The putative protein designated as core+1 is highly basic protein with a theoretical pI of 12.5, possesses several separate hydrophilic and/or antigenic domains as described below, and is likely to associate with mitochondria (PSORT program).

Calculated Molecular Weight=17285.94
Estimated pI=12.48
Amino Acid Composition:

|  | No. | Percent |
|---|---|---|
| Non-polar: | | |
| Ala | 20 | 12.05 |
| Val | 12 | 7.23 |
| Leu | 17 | 10.24 |
| Ile | 3 | 1.81 |
| Pro | 15 | 9.04 |
| Met | 4 | 2.41 |
| Phe | 2 | 1.20 |
| Trp | 5 | 3.01 |
| Polar: | | |
| Gly | 17 | 10.24 |
| Ser | 17 | 10.24 |
| Thr | 11 | 6.63 |
| Cys | 4 | 2.41 |
| Tyr | 1 | 0.60 |
| Asn | 3 | 1.81 |
| Gln | 3 | 1.81 |
| Acidic: | | |
| Asp | 3 | 1.81 |
| Glu | 4 | 2.41 |
| Basic: | | |
| Lys | 4 | 2.41 |
| Arg | 18 | 10.84 |
| His | 1 | 0.60 |

The polypeptide encoded by this novel ORF is referred to herein as core+1 protein. One embodiment of the core+1 protein is designated herein as SEQ ID NO:1. A nucleotide sequence of the invention encoding core+1 protein is designated SEQ ID NO:2.

Relevant to the findings of this invention are the following:

a) Based on the nature of the genetic code, about 70% of nucleotide changes at the $3^{rd}$ position are expected to be synonymous, whereas any changes of nucleotides at the $2^{nd}$ position are nonsynonymous. Comparison of complete genome sequences from different variants of hepatitis C virus has shown that synonymous changes are suppressed in the core region. Computer-assisted analysis of the HCV sequence has revealed a novel ORF overlapping the core in the +1 frame. Thus, synonymous substitutions (i.e. at the $3^{rd}$ position) for the core gene might be constrained to a great extent against amino acid changes of this novel ORF, should this ORF produce a protein.

b) Pestiviruses, which are considered to be the most closely related virus group to hepatitis C virus, contain a cysteine-like proteinase ($N^{pro}$) upstream of their core gene. In addition, a number of animal viruses code for proteinases, which possess a cysteine-like proteinase activity and are considered to be key components of viral genome expression. The L-proteinase of apthoviruses and the PCP1 proteinase of human coronavirus HCV 229E are such examples. In almost all cases these proteinases are encoded by sequences either upstream or downstream of the capsid precursor. Computer alignment between the amino acid sequences of core+1 protein and the $N^{pro}$ of the pestiviruses revealed partial homology between these two proteins, which is characteristic of viral cysteine proteinases. Most importantly the amino acid residues, His and Cys, which are considered to be in the catalytic site of these enzymes, are conserved in core+1 protein. Interestingly, preliminary data supporting a protease activity for the core+1 protein has been obtained.

The implications for this invention are widespread. A cDNA encoding core+1 protein has been isolated and is disclosed in SEQ ID NO:2. This discovery of the cDNA encoding core+1 protein enables construction of expression vectors comprising nucleic acid sequences encoding core+1 polypeptides; host cells transfected or transformed with the expression vectors; biologically active core+1 polypeptides and core+1 polypeptides as isolated or purified proteins; and antibodies immunoreactive with core+1 polypeptides. In addition, understanding of the mechanism by which core+1 polypeptides function enables the design of assays to detect inhibitors of core+1 protein activity.

As used herein, the term "core+1 polypeptides" refers to a genus of polypeptides that further encompasses proteins having the amino acid sequence of SEQ ID NO:1, as well as those proteins and polypeptides having a high degree of similarity (at least 90% homology) with such amino acid sequences and which proteins and polypeptides are immunoreactive. In addition, core+1 polypeptides refers to the gene products of the nucleotides of SEQ ID NO:2.

The term "purified" as used herein, means that the core+1 polypeptides are essentially free of association with other proteins or polypeptides, for example, as a purification product of recombinant host cell culture or as a purified product from a non-recombinant source. The term "substantially purified" as used herein, refers to a mixture that contains core+1 polypeptides and is essentially free of association with other proteins or polypeptides, but for the presence of known proteins that can be removed using a specific antibody, and which substantially purified core+1 polypeptides can be used as antigens.

A core+1 polypeptide "variant" as referred to herein means a polypeptide substantially homologous to native core+1 polypeptides, but which has an amino acid sequence different from that of native core+1 polypeptides because of one or more deletions, insertions, or substitutions. The variant amino acid sequence preferably is at least 80% identical to a native core+1 polypeptide amino acid sequence, most preferably at least 90% identical. The percent identity can be determined, for example by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (Adv. Appl. Math 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring core+1 polypeptide variants are also encompassed by the invention. Examples of such variants are proteins that result from alternate mRNA splicing events or from proteolytic cleavage of the core+1 polypeptides. Variations attributable to proteolysis include, for example, differences in ithe termini upon expression in different types of host cells, due to proteolytic removal of one or more terminal amino acids from the core+1 polypeptides. Variations attributable to frameshifting include, for example, differences in the termini upon expression in different types of host cells due to different amino acids of core.

As stated above, the invention provides isolated and purified, or homogeneous, core+1 polypeptides, both recombinant and non-recombinant. Variants and derivatives of native core+1 polypeptides that can be used as antigens can be obtained by mutations of nucleotide sequences coding for native core+1 polypeptides. Alterations of the native amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion, or insertion. Exemplary methods of making the alterations set forth above are disclosed by Walder et al. (Gene 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, all of which are incorporated by reference.

Within an aspect of the invention, core+1 polypeptides can be utilized to prepare antibodies that specifically bind to core+1 polypeptides. The term "antibodies" is meant to include polyclonal antibodies, monoclonal antibodies, fragments thereof such as F(ab')2 and Fab fragments, as well as any recombinantly produced binding partners. Antibodies are defined to be specifically binding if they bind core+1 polypeptides with a $K_a$ of greater than or equal to about $10^7$ $M^{-1}$. Affinities of binding partners or antibodies can be readily determined using conventional techniques, for example, those described by Scatchard et al., *Ann. N.Y Acad. Sci.*, 51:660 (1949). Polyclonal antibodies can be readily generated from a variety of sources, for example, horses, cows, goats, sheep, dogs, chickens, rabbits, mice, or rats, using procedures that are well known in the art.

The invention further encompasses isolated fragments and oligonucleotides derived from the nucleotide sequence of SEQ ID NO:2. The invention also encompasses polypeptides encoded by these fragments and oligonucleotides.

Nucleic acid sequences within the scope of the invention include isolated DNA and RNA sequences that hybridize to the native core+1 nucleic acids disclosed herein under conditions of moderate or severe stringency, and which encode core+1 polypeptides. As used herein, conditions of moderate stringency, as known to those having ordinary skill in the art, and as defined by Sambrook et al. *Molecular Cloning: A Laboratory Manual,* 2 ed. Vol. 1, pp. 1.101–104, Cold Spring Harbor Laboratory Press, (1989), include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 420° C.), and washing conditions of about 60° C., 0.5×SSC, 0.1% SDS. Conditions of high stringency are defined as hybridization conditions as above, and with washing at 68° C., 0.2×SSC, 0.1% SDS. The skilled artisan will recognize that the temperature and wash solution salt concentration can be adjusted as necessary according to factors such as the length of the probe.

Due to the known degeneracy of the genetic code, wherein more than one codon can encode the same amino acid, a DNA sequence can vary from that shown in SEQ ID NO:2 and still encode a core+1 polypeptide having the amino acid sequence of SEQ ID NO:1. Such variant DNA sequences can result from silent mutations (e.g., occurring during PCR amplification), or can be the product of deliberate mutagenesis of a native sequence.

The invention thus provides equivalent isolated DNA sequences, encoding core+1 polypeptides, selected from: (a) DNA derived from the coding region of a native core+1 gene; (b) cDNA comprising the nucleotide sequence of SEQ ID NO:2; (c) DNA capable of hybridization to a DNA of (a) under conditions of moderate stringency and which encode core+1 polypeptides; and (d) DNA which is degenerate as a result of the genetic code to a DNA defined in (a), (b) or (c) and which encodes core+1 polypeptides. Core+1 polypeptides encoded by such DNA equivalent sequences are encompassed by the invention.

DNA that is equivalent to the DNA sequence of SEQ ID NO:2 will hybridize under moderately stringent conditions to the double-stranded native DNA sequence that encode polypeptides comprising amino acid sequences of SEQ ID NO:1. Examples of core+1 polypeptides encoded by such DNA, include, but are not limited to, core+1 polypeptide fragments and core+1 polypeptides comprising inactivated N-glycosylation site(s), inactivated protease processing site (s), or conservative amino acid substitution(s), as described above. Core+1 polypeptides encoded by DNA derived from other species, wherein the DNA will hybridize to the complement of the DNA of SEQ ID NO:2 are also encompassed.

Recombinant expression vectors containing a nucleic acid sequence encoding core+1 polypeptides can be prepared using well known methods. The expression vectors include a core+1 DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the core+1 DNA sequence. Thus, a promoter nucleotide sequence is operably linked to a core+1 DNA sequence if the promoter nucleotide sequence controls the transcription of the core+1 DNA sequence. The ability to replicate in the desired host cells, usually conferred by an origin of replication, and a selection gene by which transformants are identified can additionally be incorporated into the expression vector.

In addition, sequences encoding appropriate signal peptides that are not naturally associated with core+1 polypeptides can be incorporated into expression vectors. For example, a DNA sequence for a signal peptide (secretory leader) can be fused in-frame to the core+1 nucleotide sequence so that the core+1 polypeptide is initially translated as a fusion protein comprising the signal peptide. A signal peptide that is functional in the intended host cells enhances extracellular secretion of the core+1 polypeptide. The signal peptide can be cleaved from the core+1 polypeptide upon secretion of core+1 polypeptide from the cell.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids. Commercially available vectors include those that are specifically designed for the expression of proteins. These include pMAL-p2 and pMAL-c2 vectors, which are used for the expression of proteins fused to maltose binding protein (New England Biolabs, Beverly, Mass., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776), and tac promoter (Maniatis, *Molecular Cloning: A Laboratory Manual*, Cold Spring Harbor Laboratory, p. 412, 1982).

Suitable host cells for expression of core+1 polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce core+1 polypeptides using RNAs derived from DNA constructs disclosed herein.

It will be understood that the present invention is intended to encompass the previously described proteins in isolated or purified form, whether obtained using the techniques described herein or other methods. In a preferred embodiment of this invention, the core+1 polypeptides are substantially free of human tissue and human tissue components, nucleic acids, extraneous proteins and lipids, and adventitious microorganisms, such as bacteria and viruses. It will also be understood that the invention encompasses equivalent proteins having substantially the same biological and immunogenic properties. Thus, this invention is intended to cover serotypic variants of the proteins of the invention.

Depending on the use to be made of the core+1 polypeptides of the invention, it may be desirable to label them. Examples of suitable labels are radioactive labels, enzymatic labels, fluorescent labels, chemiluminescent labels, and chromophores. The methods for labeling proteins and glycoproteins of the invention do not differ in essence from those widely used for labeling immunoglobulin. The need to label may be avoided by using labeled antibody to the antigen of the invention or anti-immunoglobulin to the antibodies to the antigen as an indirect marker.

Once the core+1 polypeptides of the invention have been obtained, they can be used to produce polyclonal and monoclonal antibodies reactive therewith. Thus, a protein or polypeptide of the invention can be used to immunize an animal host by techniques known in the art. Such techniques usually involve inoculation, but they may involve other modes of administration. A sufficient amount of the protein or the polypeptide is administered to create an immunogenic response in the animal host. Any host that produces antibodies to the antigen of the invention can be used. Once the animal has been immunized and sufficient time has passed for it to begin producing antibodies to the antigen, polyclonal antibodies can be recovered. The general method comprises removing blood from the animal and separating the serum from the blood. The serum, which contains antibodies to the antigen, can be used as an antiserum to the antigen. Alternatively, the antibodies can be recovered from the serum. Affinity purification is a preferred technique for recovering purified polyclonal antibodies to the antigen, from the serum.

Monoclonal antibodies to the antigens of the invention can also be prepared. One method for producing monoclonal antibodies reactive with the antigens comprises the steps of immunizing a host with the antigen; recovering antibody producing cells from the spleen of the host; fusing the antibody producing cells with myeloma cells deficient in the enzyme hypoxanthine-guanine phosphoribosyl transferase to form hybridomas; select at least one of the hybridomas by growth in a medium comprising hypoxanthine, aminopterin, and thymidine; identifying at least one of the hybridomas that produces an antibody to the antigen, culturing the identified hybridoma to produce antibody in a recoverable quantity; and recovering the antibodies produced by the cultured hybridoma.

These polyclonal or monoclonal antibodies can be used in a variety of applications. Among these is the neutralization of corresponding proteins. They can also be used to detect viral antigens in biological preparations or in purifying corresponding proteins, glycoproteins, or mixtures thereof, for example when used in a affinity chromatographic columns.

The core+1 polypeptides can be used as antigens to identify antibodies to HCV in materials and to determine the concentration of the antibodies in those materials. Thus, the antigens can be used for qualitative or quantitative determination of the virus in a material. Such materials of course include human tissue and human cells, as well as biological fluids, such as human body fluids, including human sera. When used as a reagent in an immunoassay for determining the presence or concentration of the antibodies to HCV, the antigens of the present invention provide an assay that is convenient, rapid, sensitive, and specific.

More particularly, the antigens of the invention can be employed for the detection of HCV by means of immunoassays that are well known for use in detecting or quantifying humoral components in fluids. Thus, antigen-antibody interactions can be directly observed or determined by secondary reactions, such as precipitation or agglutination. In addition, immunoelectrophoresis techniques can also be employed. For example, the classic combination of electrophoresis in agar followed by reaction with anti-serum can be utilized, as well as two-dimensional electrophoresis, rocket electrophoresis, and immunolabeling of polyacrylamide gel patterns (Western Blot or immunoblot). Other immunoassays in which the antigens of the present invention can be employed include, but are not limited to, radioimmunoassay, competitive immunoprecipitation assay, enzyme immunoassay, and immunofluorescence assay. It will be understood that turbidimetric, calorimetric, and nephelometric techniques can be employed. An immunoassay based on Western Blot technique is preferred.

Immunoassays can be carried out by immobilizing one of the immunoreagents, either an antigen of the invention or an antibody of the invention to the antigen, on a carrier surface while retaining immunoreactivity of the reagent. The reciprocal immunoreagent can be unlabeled or labeled in such a manner that immunoreactivity is also retained. These techniques are especially suitable for use in enzyme immunoassays, such as enzyme linked immunosorbent assay (ELISA) and competitive inhibition enzyme immunoassay (CIEIA).

When either the antigen of the invention or antibody to the antigen is attached to a solid support, the support is usually a glass or plastic material. Plastic materials molded in the form of plates, tubes, beads, or disks are preferred. Examples of suitable plastic materials are polystyrene and polyvinyl chloride. If the immunoreagent does not readily bind to the solid support, a carrier material can be interposed between the reagent and the support. Examples of suitable carrier materials are proteins, such as bovine serum albumin, or chemical reagents, such as gluteraldehyde or urea. Coating of the solid phase can be carried out using conventional techniques.

The invention provides immunogenic core+1 polypeptides, and more particularly, protective polypeptides for use in the preparation of vaccine compositions against HCV. These polypeptides can thus be employed as viral vaccines by administering the polypeptides to a mammal susceptible to HCV infection. Conventional modes of administration can be employed. For example, administration can be carried out by oral, respiratory, or parenteral routes. Intradermal, subcutaneous, and intramuscular routes of administration are preferred when the vaccine is administered parenterally.

The major purpose of the immune response in an HCV-infected mammal is to inactivate the free HCV virus and to eliminate HCV infected cells that have the potential to release infectious virus. The B-cell arm of the immune response has the major responsibility for inactivating free HCV virus. The principal manner in which this is achieved is by neutralization of infectivity. Another major mechanism for destruction of the HCV-infected cells is provided by cytotoxic T lymphocytes (CTL) that recognize viral core+1 antigens expressed in combination with class I histocompatibility antigens at the cell surface. The CTLs recognize core+1 polypeptides processed within cells from a core+1 protein that is produced, for example, by the infected cell or that is internalized by a phagocytic cell. Thus, this invention can be employed to stimulate a B-cell response to core+1 polypeptides, as well as immunity mediated by a CTL response following viral infection. The CTL response can play an important role in mediating recovery from primary HCV infection and in accelerating recovery during subsequent infections.

The ability of the core+1 polypeptides and vaccines of the invention to induce protective levels of neutralizing antibody in a host can be enhanced by emulsification with an adjuvant, incorporating in a liposome, coupling to a suitable carrier, or by combinations of these techniques. For example, the core+1 polypeptides of the invention can be administered with a conventional adjuvant, such as aluminum phosphate and aluminum hydroxide gel, in an amount sufficient to potentiate humoral or cell-mediated immune response in the host. Similarly, the core+1 polypeptides can be bound to lipid membranes or incorporated in lipid membranes to form liposomes. The use of nonpyrogenic lipids free of nucleic acids and other extraneous matter can be employed for this purpose.

The immunization schedule will depend upon several factors, such as the susceptibility of the host to infection and the age of the host. A single does of the vaccine of the invention can be administered to the host or a primary course of immunization can be followed in which several doses at intervals of time are administered. Subsequent doses used as boosters can be administered as need following the primary course.

The core+1 proteins, polypeptides, and vaccines of the invention can be administered to the host in an amount sufficient to prevent or inhibit HCV infection or replication in vivo. In any event, the amount administered should be at least sufficient to protect the host against substantial immunosuppression, even though HCV infection may not be entirely prevented. An immunogenic response can be obtained by administering the proteins or glycoproteins of the invention to the host in an amount of about 10 to about 500 micrograms antigen per kilogram of body weight, preferably about 50 to about 100 micrograms antigen per kilogram of body weight. The proteins and vaccines of the invention can be administered together with a physiologically acceptable carrier. For example, a diluent, such as water or a saline solution, can be employed.

Another aspect of the invention provides a method of DNA vaccination. The method also includes administering any combination of the nucleic acids encoding core+1 polypeptides, the proteins and polypeptides per se, with or without carrier molecules, to an individual. In embodiments, the individual is an animal, and is preferably a mammal. More preferably, the mammal is selected from the group consisting of a human, a dog, a cat, a bovine, a pig, and a horse. In an especially preferred embodiment, the mammal is a human.

The methods of treating include administering immunogenic compositions comprising core+1 polypeptides, but compositions comprising nucleic acids encoding core+1 polypeptides as well. Those of skill in the art are cognizant of the concept, application, and effectiveness of nucleic acid vaccines (e.g., DNA vaccines) and nucleic acid vaccine technology as well as protein and polypeptide based technologies. The nucleic acid based technology allows the administration of nucleic acids encoding core+1 polypeptides, naked or encapsulated, directly to tissues and cells without the need for production of encoded proteins prior to administration. The technology is based on the ability of these nucleic acids to be taken up by cells of the recipient organism and expressed to produce an immunogenic determinant to which the recipient's immune system responds. Typically, the expressed antigens are displayed on the surface of cells that have taken up and expressed the nucleic acids, but expression and export of the encoded antigens into the circulatory system of the recipient individual is also within the scope of the present invention. Such nucleic acid vaccine technology includes, but is not limited to, delivery of naked DNA and RNA and delivery of expression vectors encoding core+1 polypeptides. Although the technology is termed "vaccine", it is equally applicable to immunogenic compositions that do not result in a protective response. Such non-protection inducing compositions and methods are encompassed within the present invention.

Although it is within the present invention to deliver nucleic acids encoding core+1 polypeptides and carrier molecules as naked nucleic acid, the present invention also encompasses delivery of nucleic acids as part of larger or more complex compositions. Included among these delivery systems are viruses, virus-like particles, or bacteria containing the nucleic acid encoding core+1 polypeptides. Also, complexes of the invention's nucleic acids and carrier molecules with cell permeabilizing compounds, such as liposomes, are included within the scope of the invention. Other compounds, such as molecular vectors (EP 696,191, Samain et al.) and delivery systems for nucleic acid vaccines are known to the skilled artisan and exemplified in, for example, WO 93 06223 and WO 90 11092, U.S. Pat. Nos. 5,580,859, and 5,589,466 (Vical's patents), which are incorporated by reference herein, and can be made and used without undue or excessive experimentation.

To further achieve the objects and in accordance with the purposes of the present invention, a kit capable of diagnosing an HCV infection is described. This kit, in one embodiment, contains the DNA sequences of this invention, which are capable of hybridizing to viral RNA or analogous DNA sequences to indicate the presence of an HCV infection. Different diagnostic techniques can be used which include, but are not limited to:

(1) Southern blot procedures to identify cellular DNA which may or may not be digested with restriction enzymes; (2) Northern blot techniques to identify RNA extracted from cells; and (3) dot blot techniques, i.e., direct filtration of the sample through an ad hoc membrane, such as nitrocellulose or nylon, without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by centrifugation.

This invention will be described in greater detail in the following Examples.

EXAMPLE 1

The strategy for testing whether the core+1 ORF is functional, is based on the ability of most of HCV proteins to induce antibodies in HCV infected patients. Thus, the putative polypeptide was expressed in *E. coli* as a fusion protein and used as antigen to screen human sera from HCV infected patients for the existence of circulating antibodies against it.

Figure 1A:
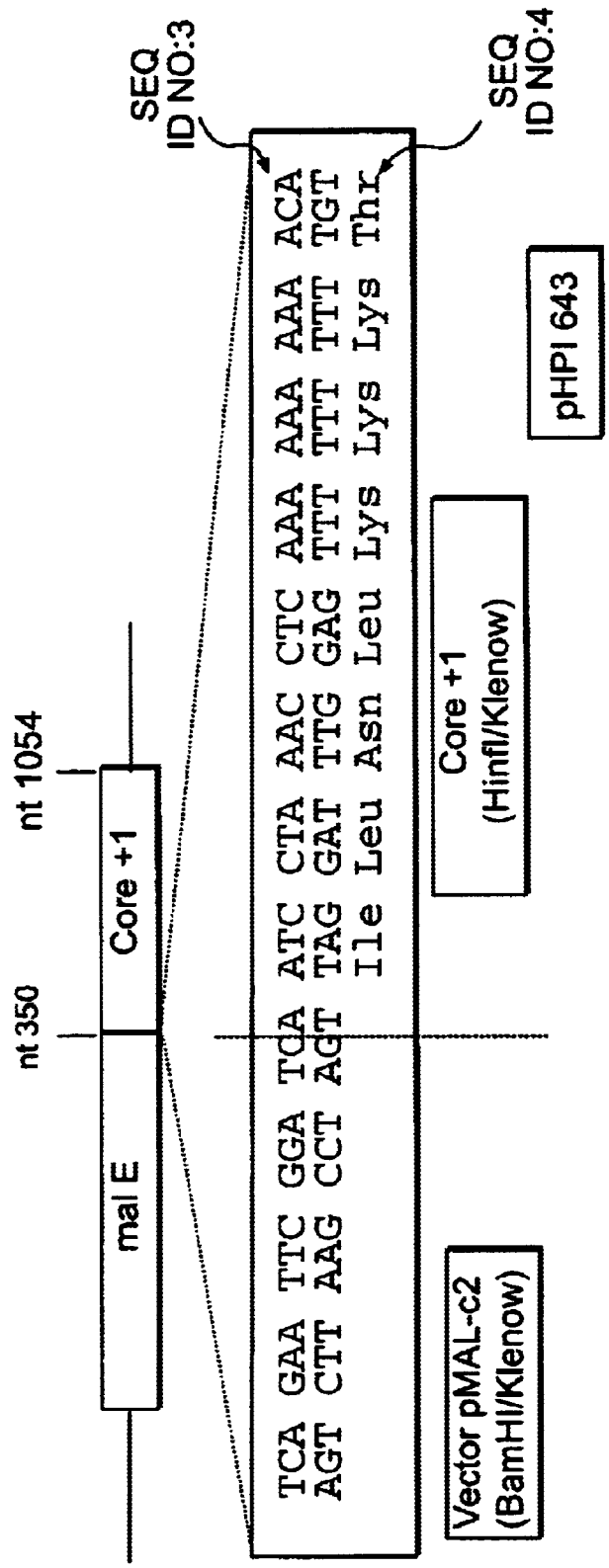
FIG. 1 describes two plasmids of the invention, pHPI 643, (SEQ ID NOS: 3 and 4) and pHPI 644 (SEQ ID NOS: 5 and 6).
Figure 1B:
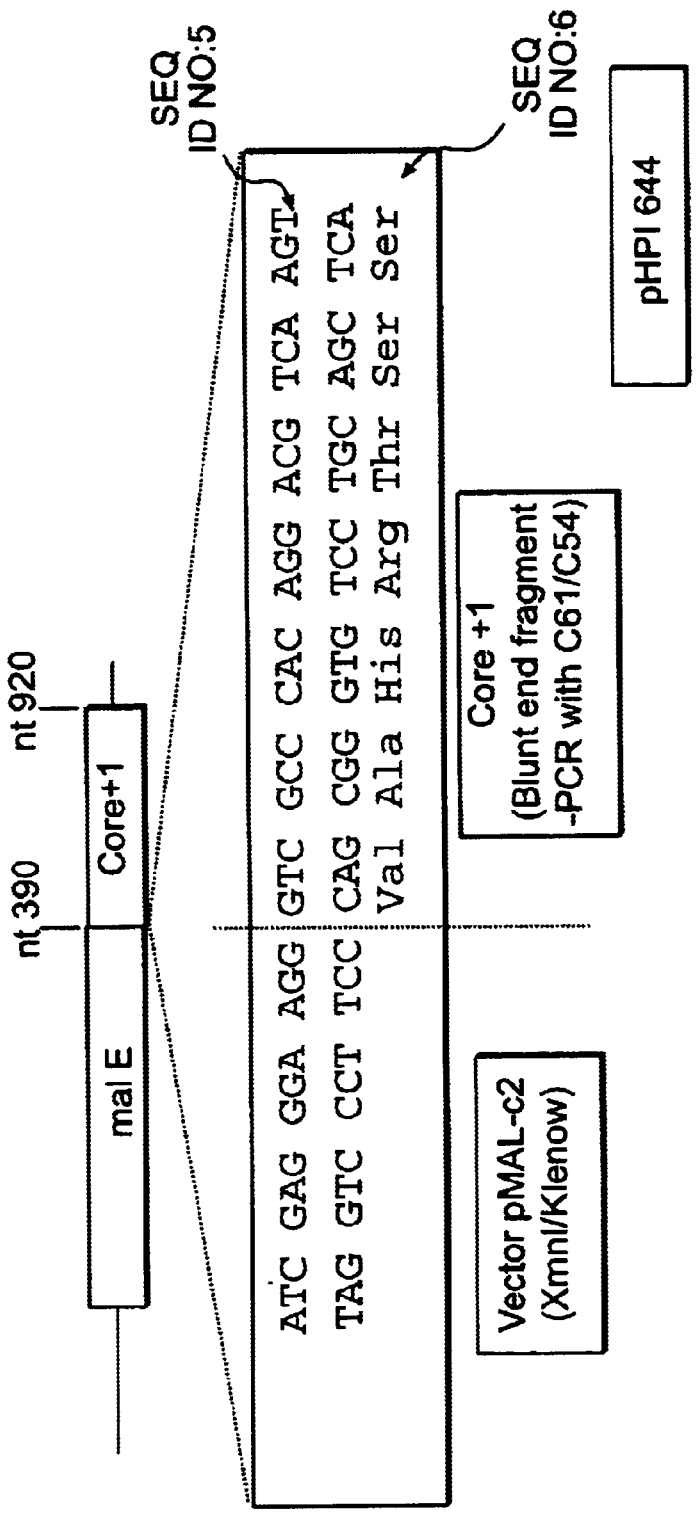

As a first step the nucleotide sequence 350–1054 was cloned into the pmal-c2 expression vector, resulting in plasmid pHPI 643 (FIG. 1; panel A (SEQ ID NOS: 3 and 4)). Sequencing of this plasmid confirmed the correct frame between the maltose-binding protein and core+1. The fused malE-core+1(L) protein had a calculated MW of ~60 kDa.

This recombinant protein was expressed in *E. coli* after induction with 0.5 mM IPTG and was tested by Western blot analysis using anti-mal antiserum and HCV-positive human serum. As shown in FIG. 2, in the cell lysates harboring the pmal-c2 vector, a protein band of 47 kDa corresponding to the mal E protein alone was detectable with the anti-mal polyclonal antiserum (FIG. 2; panel A; lanes 3 and 4). This band was not detectable when the HCV-positive human serum was used (FIG. 2; panel B; lanes 3 and 4).

In contrast, the cell lysates harboring plasmid pHPI 643 reacted with human serum specifically. Four protein bands appeared with apparent MW within the range of 45 to 58 kDa (FIG. 2; panel B; lanes 5 and 6). On the other hand only a single polypeptide with apparent MW of 43 kDa was detected when the anti-mal antiserum was used (FIG. 2; panel A; lanes 5 and 6). These results indicate that the pHPI 643 plasmid produces a protein, which is recognized by HCV positive human serum. However, the difference in the MW of the protein recognized by the anti-mal and the human serum remains obscure.

Taken together, these results indicate that 1) the pHPI 643 plasmid (SEQ ID NO: 3) produces a protein (SEQ ID NO: 4) that is recognized by the HCV-positive human serum and 2) the majority of the recombinant protein is degraded or specifically cleaved near the fusion site resulting in the apparent discrepancies between the calculated and apparent MW of the protein.

EXAMPLE 2

In an effort to overcome the degradation/processing or specific cleavage of the fusion protein, a second plasmid was constructed (pHPI 644) (FIG. 1; panel B (SEQ ID NOS: 5 and 6)), which was designed to produce a malE-core+1(S) fusion protein truncated by 13 aa at the amino terminus of the putative core+1 protein. The reason for this deletion was to avoid sequences of the amino terminal region of the core gene, which were suspected to have an effect on the stability of the protein.

As shown in FIG. 2, a protein with apparent MW of about 58 kDa was detected in pHI 644 transformed *E. coli* lysates when anti-mal antiserum was used (panel A; lanes 7 and 8). In addition, specific protein bands ranging from 45–58 kDa were detectable when HCV-positive human serum was used (panel B; lanes 7 and 8), indicating the presence of anti-core+1 antibodies in the HCV-positive serum. It should be noted that the calculated MW of mal-core+1(S) protein is about 58 kDa. Therefore, the lack of the first 13 amino acids from the amino terminus of core+1 ORF overcome the degradation/processing or cleavage problem and result in the synthesis of an intact form of the fusion protein in *E. coli*.

Additionally, a panel of previously characterized HCV-positive and negative human sera was used to evaluate the reactivity of the truncated protein against HCV circulating antibodies. As shown in FIG. 3, out of twelve HCV-positive sera, nine reacted strongly with the truncated core+1(S) protein (FIG. 3; panel A; lanes 2, 6, 8, 10, 12, 14, 16, 18, and 20), one reacted poorly (FIG. 3; panel B; lane 5), and one HCV positive serum did not have any antibodies against core+1(S) protein (FIG. 3; panel B; lane 8). Furthermore, three out of three HCV-negative sera were also negative to core+1 (S) truncated protein (FIG. 3; panel B; lanes 2, 8, 11, and 14), indicative of the specificity of this recombinant antigen for HCV antibodies.

Taken together these data indicate that HCV-positive patients produce antibodies against the core+1 polypeptide supporting the expression of the novel ORF from HCV viral genome during infection. However the discrepancies in the MW of the malE-core+1 recombinant antigens as shown by the anti-mal and human serum remains puzzling.

EXAMPLE 3

To test whether the problem with the differences in the MW was related to the properties of the pmal-c2 expression vector, two additional core+1 chimeric proteins were produced using the pGEX-3x expression vector. Plasmid pHPI 663 contains nt 345–774 from the core coding region (FIG. 4; panel A (SEQ ID NOS: 7 and 8)) and produces a GST-core+1(L) recombinant protein with a calculated MW of 41 kDa. Plasmid pHPI 668 contains nt 390–920 from the core coding region and produces a GST-core+1(S) recombinant protein truncated by 9 amino acids at the amino terminal of core+1 with regard to pHPI 663 (FIG. 4; panel B (SEQ ID NOS: 9 and 10)). This truncated GST-core+1(S) protein has a calculated MW of 41 kDa. Sequencing of both plasmids confirmed the correct frame between the glutathione-S-transferase and core+1 protein.

As shown in FIG. 5, in the cell lysates harboring the pGEX-3x vector, a protein band of 25 kDa corresponding to the GST protein alone was detectable with the anti-GST polyclonal antiserum (FIG. 5; lane 3). This protein was not detectable when the HCV-positive human serum was used (FIG. 5; lane 9).

When cell lysates harboring plasmid pHPI 663 were tested with the anti-GST antiserum, a protein band with an apparent MW of 25 kDa was described, instead of the expected 41 kDa (FIG. 5; lane 2), indicating extensive degradation/processing of the recombinant protein. In contrast, when HCV-positive human serum was used, four specific protein bands appeared in a range of MW from 25 to 35 kDa (FIG. 5; lane 8). These protein bands were absent from the lysates harboring the pGEX-3x vector when they were tested with the same HCV-positive human serum. Therefore, the behavior of GST-core+1(L) was similar to that of malE-core+1(L).

Moreover, when lysates harboring plasmid pHPI 668 (GST-core+1(S)) were tested in a Western blot analysis using anti-GST antiserum, a predominant protein band of about 41 kDa corresponding to the fused GST-core+1 protein was present (FIG. 5; lane 1). The size of the protein band was similar to the calculated MW (41 kDa). Several other smaller bands(29–42 kDa), probably the result of protein degradation, reacted to the polyclonal serum. Among them a specific protein band of 33 kDa was the most pronounced (FIG. 5; lane 1).

When the same lysates were tested with an HCV-positive human serum, several specific bands ranging from 29–42 kDa were present (FIG. 5; lane 7), with the most predominant ones at MW of 33 kDa, and were absent from lysates harboring the pGEX-3x vector (FIG. 5; lane 9). The same lysates were also tested against an HCV-negative human serum (FIG. 5; lane 4 and 6), showing again the specificity of the recombinant GST-core+1 protein for HCV antibodies.

These results indicate that the deletion of the first 9 amino acids of the core+1 protein results in the expression of an intact core+1 chimeric protein (as shown by anti-GST serum), which specifically react against HCV positive human serum. Taken together, these results indicate that the degradation/processing or specific cleavage of the recombinant protein is directly associated with the presence of the first 9–13 amino acids and is not dependent on the vector sequences. These data, combined with our knowledge for the pestivirus genomic organization, strongly suggest the presence of (auto)proteolytic activity for the core+1 protein.

EXAMPLE 4

A screening was also performed with a panel of previously characterized HCV-positive human sera in order to evaluate the reactivity of the GST-core+1 protein against HCV circulating antibodies. Five out of five HCV-positive human sera tested strongly reacted both with the large (FIG. 6; lanes 5, 14, 17, 20, and 23) and with the truncated form of the fused protein (FIG. 6; lanes 6, 15, 18, 21, and 24). A previously characterized HCV negative human serum was also used against these two constructs. The serum was negative for the presence of core+1 protein. This indicates the specificity of these recombinant antigens to HCV antibodies.

Even though the amino acid alignment between core+1 and core protein showed no similarity, we wanted to rule out the possibility that core+1 possesses common epitopes with the core protein. For this reason E. coli lysates harboring plasmids pHPI 643 (malE-core+1-L), pHPI 644 (malE-core+1-S), pHPI 663 (GST-core+1-L), and pHPI 668 (GST-core+1-S) were tested with a monoclonal antibody against HCV core protein by Western blot analysis. Recombinant HCV malE-core or GST-core protein was also tested for comparison. As expected the malE-core fusion protein corresponding to a specific band of 66 kDa was recognized by the core monoclonal antibody (FIG. 7; panel A; lane 12), whereas fused malE-core+1 fusion proteins, expressed from pHPI 643 and pHPI 644, were not reactive (FIG. 7; panel A; lanes 10 and 11). Both the anti-mal antiserum and sera from patients recognized the corresponding proteins similarly to the previous data (FIG. 7; panel A; lanes 3 and 4 and 6 and 7, respectively). Interestingly, however, when ECL-chemiluminescence detection was used to analyze the reactivity of the core Mab, a protein band of about 47 kDa was observed in lysates harboring pHPI 643, and a faint band, which migrated slightly faster in lysates harboring pHPI 644 (FIG. 7; panel A; lanes 14 and 15) suggesting that in addition to the core+1 protein, plasmids pHPI 643 and pHPI 644 produce, albeit in small quantities, an additional protein reactive to core monoclonal antibody. Similarly, the GST-core fusion protein corresponding to a specific band of approximately 40 kDa was recognized by the core monoclonal antibody (FIG. 7; panel B; lane 12), whereas the GST-core+1 fusion proteins, expressed from pHPI 663 and pHPI 668, were not recognized (FIG. 7; panel B; lanes 10 and 11). Both the anti-GST antiserum and sera from patients recognized the corresponding proteins (FIG. 7; panel B; lanes 3 and 4 and 6 and 7, respectively). Again, when ECL-chemiluminescence detection was used, we also observed a protein band of about 30 kDa in lysates harboring pHPI 663 and a band of about 28 kDa in lysates harboring pHPI 668.

These results were unexpected but remain reproducible. The nature of these core-related proteins and the details of the molecular mechanism responsible for their synthesis are under intensive investigation. Preliminary evidence suggests that these proteins contain the malE- of GST-protein fused in frame with about 45–50 aa from the HCV coding sequences, which are likely to share both core+1 and core amino acid motifs. Should this be the case, these data support the presence of novel mechanism(s) for translation, which account for the shift in E. coli. Such hypothetical mechanism may account also for the termination of translation of this protein since a stop codon is present in the +2 frame at nt 468–470, thus allowing the synthesis of a protein of the observed MW. Alternatively, the size of this protein may be related to proteolytic cleavage.

Preliminary Mutagenesis Studies Support the Presence of Novel RNA Signals

We analyzed the effect of a series of mutations generated within plasmid pHPI 643 or plasmid pHPI 663 by PCR. The mutated nucleotides, the amino acid changes in core+1, and the name of the generated plasmids are shown in the following Table.

| Mutations | Nucleotides | Amino Acids | Plasmids |
| --- | --- | --- | --- |
| Mut R1 | nt 398 (A → T) | His → Leu | pHPI 676 |
| Mut R2 | nt 450/451 T → C, G → C) | Cys → Ser | pHPI 679 |
| Mut R3 | nt 398 and nt 450/451 (A → T, & T → C, G → C) | His → Leu & Cys → Ser | pHPI 719 |
| Mut R4 | nt 448/451 (T → G, T → G) | Cys-Cys → Gly-Gly | pHPI 720 |
| Mut R5 | nt 450 T → A) | Cys → stop codon | pHPI 721 |

As a first step, the effect of these mutations in the synthesis of the GST-core+1-L protein and the 30 kDa core-related protein band were analyzed by Western blot analysis. All mutations had no effect in the expression of the GST-core+1-L fusion protein (FIG. 8 and data not shown). However, pHPI 720 (mut R4) and pHPI 721 (mut R5) reproducibly synthesized reduced amount of the core-related 30 kDa protein (FIG. 8; lanes 11 and 12). The effect was more severe with pHPI 720 (mut R4) (FIG. 8; lane 11).

Figure 10A:
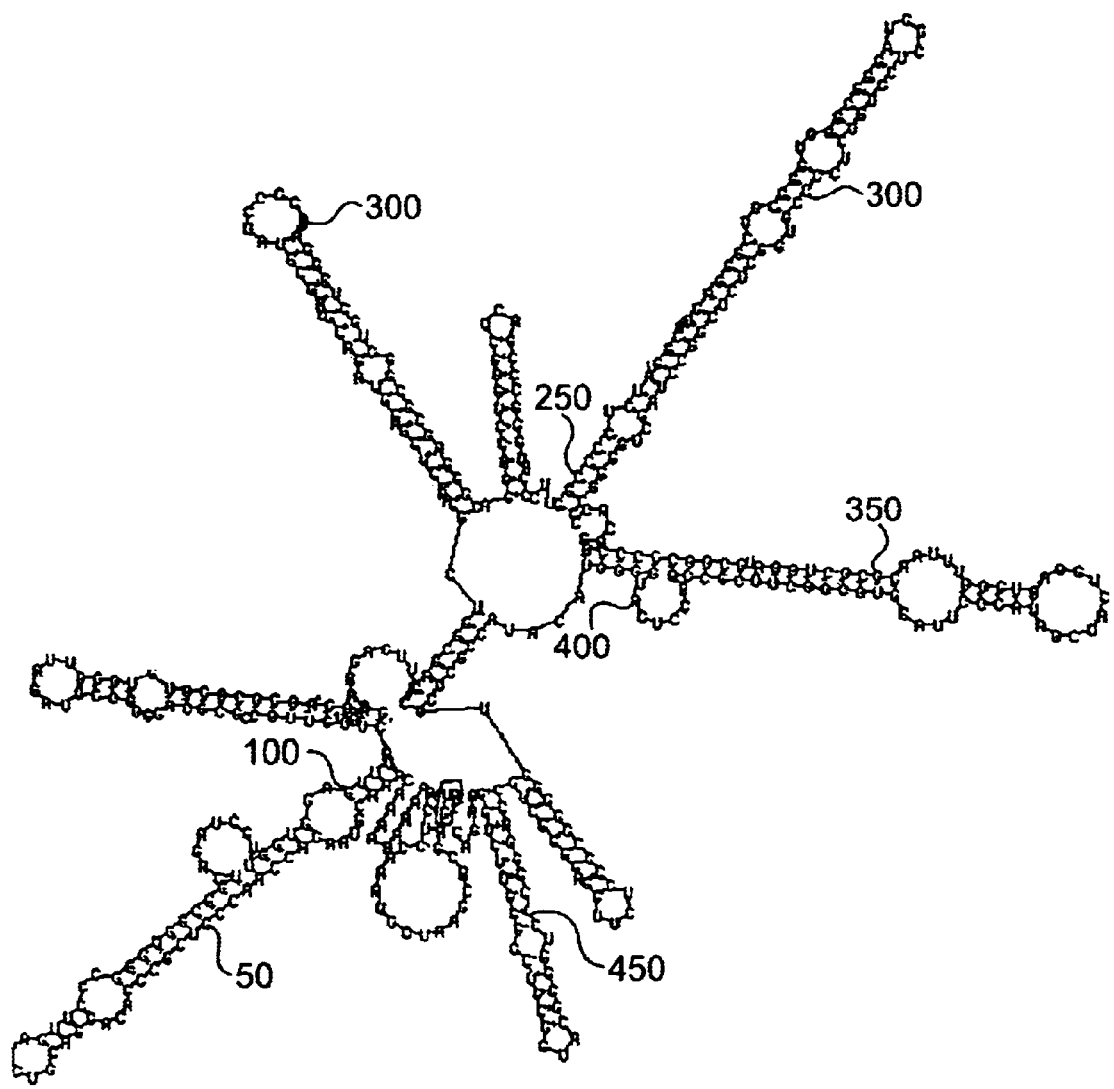
Figure 10B:
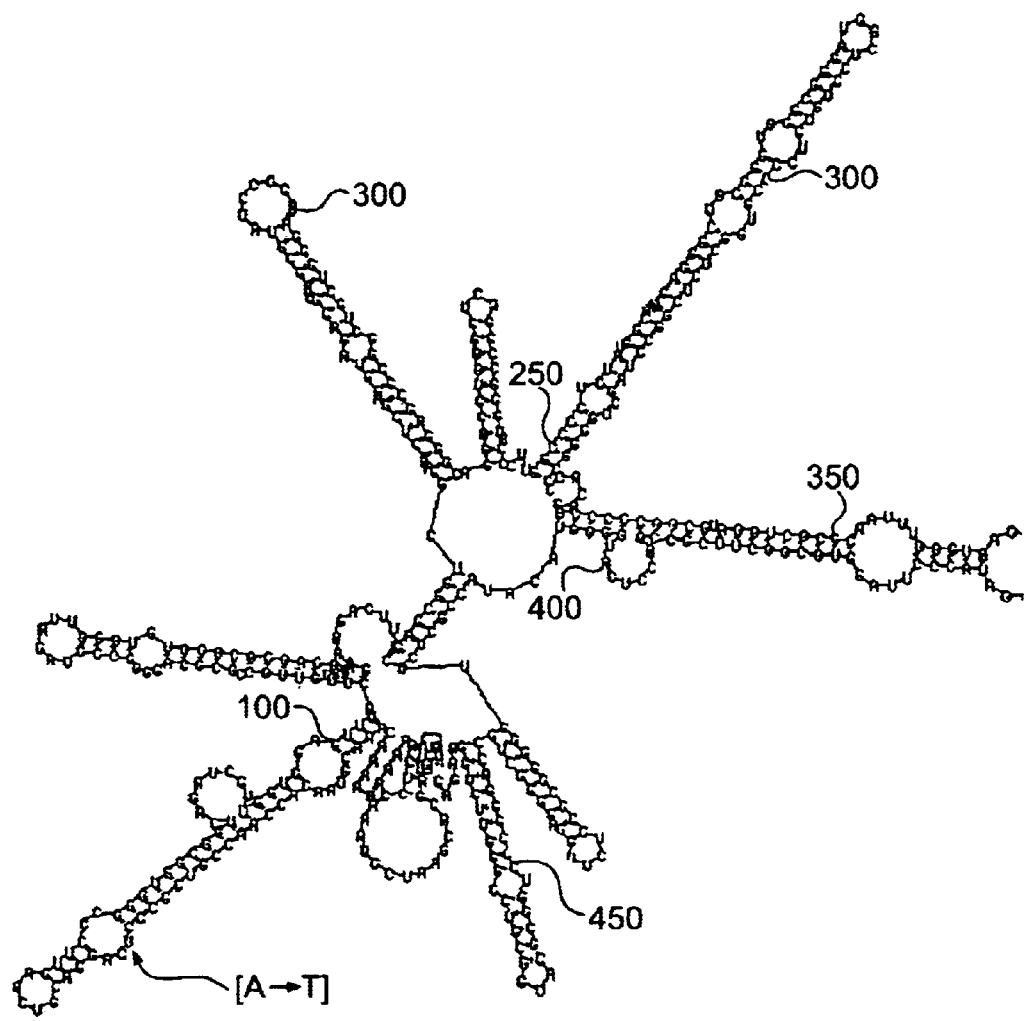
Figure 10C:
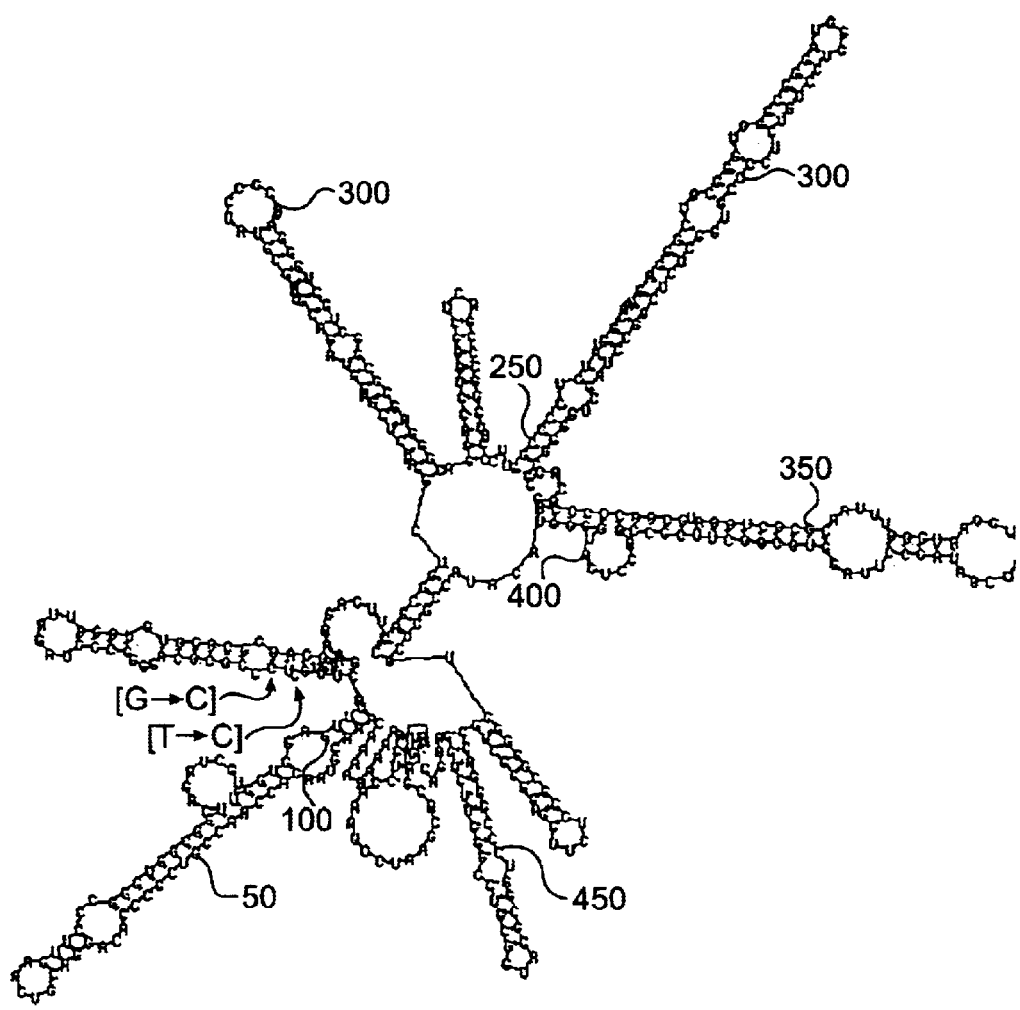
Figure 10D:
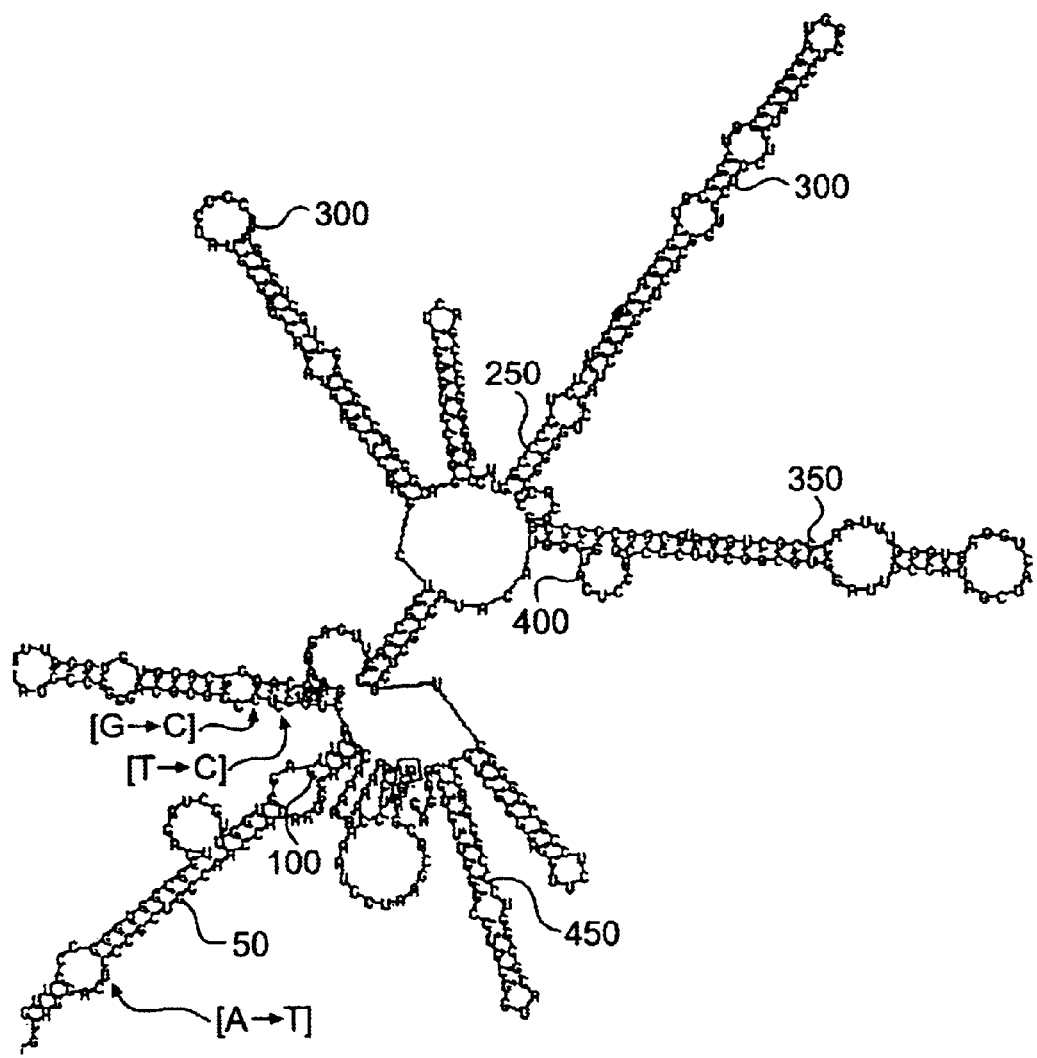
Figure 10E:
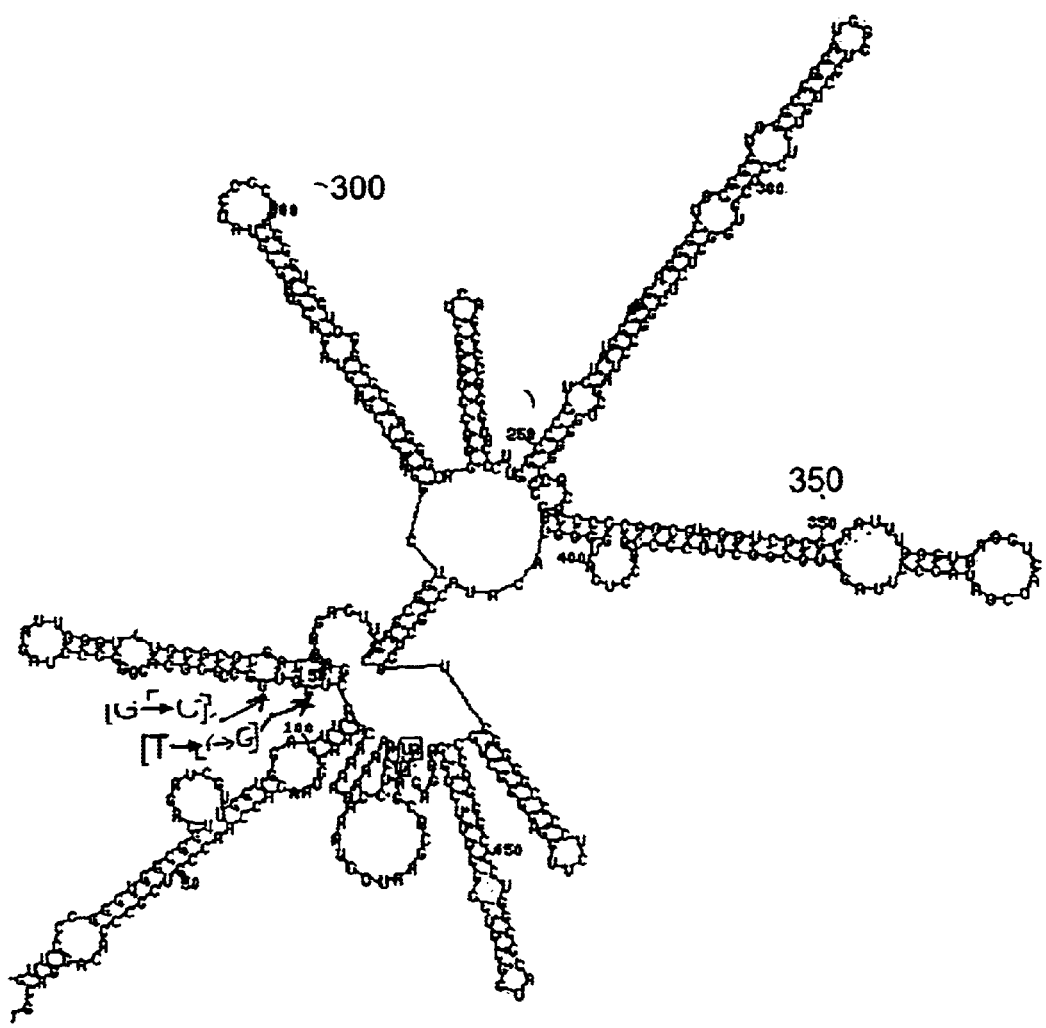
Figure 10F:
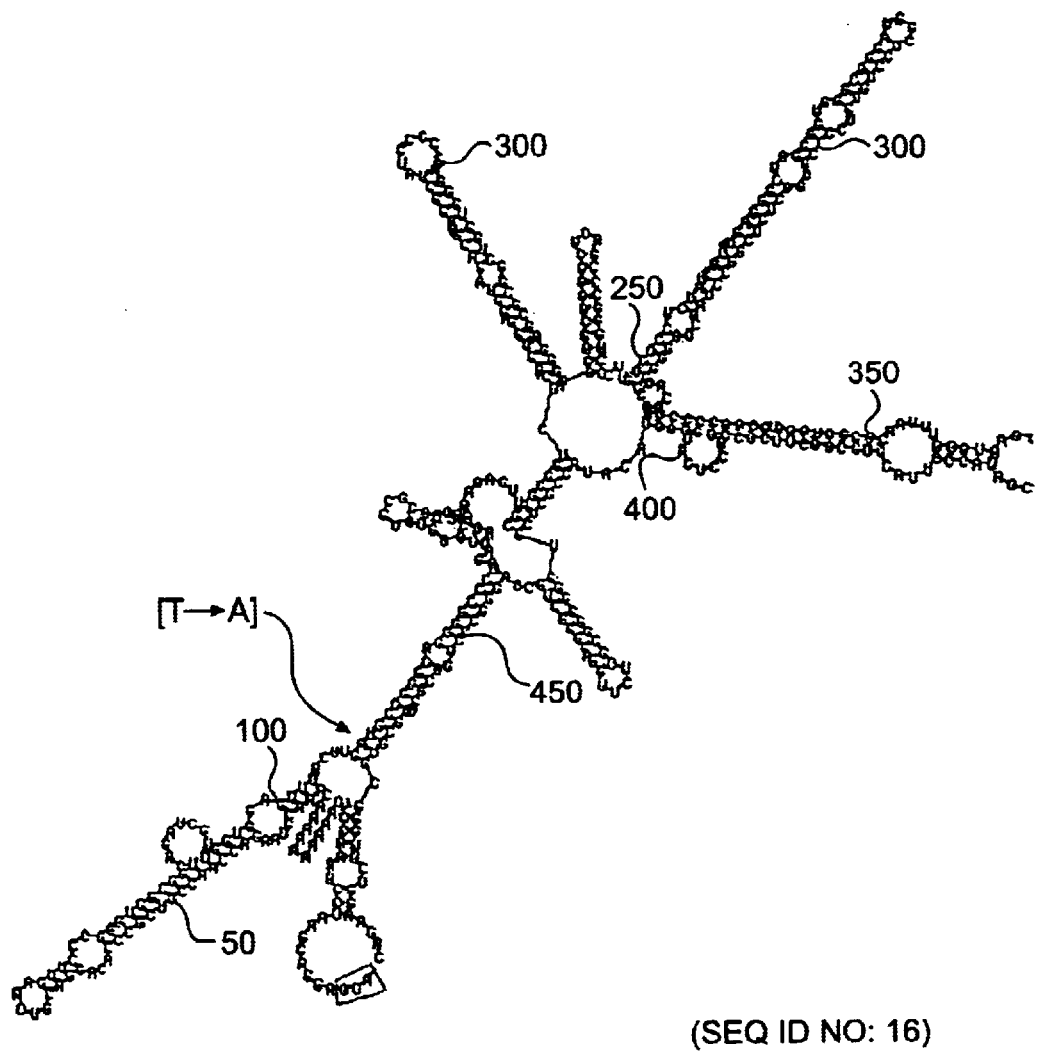

In an attempt to analyze these data, we examined the secondary RNA structure of nt 342–830 by the MFOLD program. As shown in FIG. 10a (SEQ ID NO: 11), this program predicts an extensive secondary structure within this region. Interestingly, mut R1, mut R2, and mut R3 (FIGS. 10b (SEQ ID NO: 12), 10c (SEQ ID NO: 13), and 10d (SEQ ID NO: 14)) predict minimum changes in the RNA secondary structure, whereas mut R4 and mut R5 are predicted to cause a rather severe effect on the RNA folding pattern (FIGS. 10e (SEQ ID NO: 15) and 10f (SEQ ID NO: 16)). Thus, there appears to be a rather direct correlation between the RNA secondary structure and the synthesis of the core-related 30 kDa protein band.

At the moment, the interpretation of these results are rather speculative. However, we propose the presence of novel RNA elements, which can direct or control the shift of the ribosomes in alternative reading frames.

Purification of GST-core+1 Protein, Production of Anti-core+1 Antisera

The GST-core+1 protein fusion protein was purified from cell lysates by electroelution and was characterized using Western blot analysis. As shown in FIG. 9, the purified GST-core+1 protein had the expected MW (FIG. 9, panel C, lane 3), and also reacted specifically against the polyclonal anti-GST antiserum (FIG. 9, panel A, lane 2; panel B, lane 8), and against the HCV-positive human serum (FIG. 9, panel A, lane 5; panel B, lane 5), providing further support to the specificity of this recombinant antigen to HCV antibodies. This purified GST-core+1 protein is currently being used in order to raise a polyclonal antiserum against core+1 protein in rabbits.

SUMMARY—CONCLUSIONS

1. Sequence analysis has indicated the presence of an alternative ORF (maximum length 160 aa) within nt 344 to 830 in the +1 reading frame.

2. Our data strongly supports that this novel ORF is functional inasmuch as sera from HCV-infected patients contain antibodies against recombinant core+1 (C1) protein expressed in *E. coli*, while sera from uninfected individuals do not.

3. Preliminary evidence indicated that the *E. coli* core+1 (C1) protein has protease activity and/or autoproteolytic activity. This function appears to correlate with the presence of the first 9 aa (nt 350 to 380). Moreover, sequence analysis has revealed the existence of conserved motifs containing the catalytic His and Cys as between the $N^{pro}$ protease of the pestiviruses and the core+1 protein.

4. Preliminary evidence suggests the presence of novel RNA signals responsible for the reading of ribosomes from alternative frames.

5. Computer analysis strongly predicts an association of the core+1 protein with mitochondria (PSORT computer program).

6. Finally, it should be noted that some of the functions of the core protein (such as transactivation, apoptosis or steatosis) may be attributed to core+1 protein inasmuch as both proteins are expected to be expressed in these experiments. Interestingly, steatosis is directly related to damage of mitochondria. According to the PSORT program, core+1 has a stronger probability for localization in the mitochondria than the core protein.

The following plasmids were deposited at the Collection Nationale de Cultures de Microorganismes (C.N.C.M.), of Institut Pasteur, 28, rue du Docteur Roux, F-75724 Paris, Cedex 15, France, on Aug. 26, 1999, and assigned the following Accession Nos.:

| PLASMID | ACCESSION NO. |
| --- | --- |
| XL-1/pHPI 643 | I-2295 |
| XL-1/pHPI 644 | I-2296 |
| XL-1/pHPI 663 | I-2297 |
| XL-1/pHPI 668 | I-2298 |
| XL-1/pHPI 676 | I-2299 |
| XL-1/pHPI 679 | I-2303 |
| XL-1/pHPI 719 | I-2300 |
| XL-1/pHPI 720 | I-2301 |
| XL-1/pHPI 721 | I-2302 |

REFERENCES

The entire disclosures of each of the following publications are relied upon and incorporated by reference herein.

Behrens, S. E., Tomei, L., and De Francesco, R. (1996), "Identification and properties of the RNA-dependent RNA polymerase of hepatitis C virus", *Embo J.* 15:12–22.

Chien, D. Y., Choo, Q. L., Ralston, R., Spaete, R., Tong, M., Houghton, M., and Kuo, G. (1993), "Persistence of HCV despite antibodies to both putative envelope glycoproteins", *Lancet* 342:933.

Dubuisson, J., Hsu, H. H., Cheung, R. C., Greenberg, H. B., Russell, D. G., and Rice, C. M. (1994), "Formation and intracellular localization of hepatitis C virus envelope glycoprotein complexes expressed by recombinant vaccinia and Sindbis viruses", *J. Virol.* 68:6147–60.

Failla, C., Tomei, L., and De Francesco, R. (1995), "An amino-terminal domain of the hepatitis C virus NS3 protease is essential for interaction with NS4A", *J. Virol.* 69:1769–77.

Grakoui, A., Wychowski, C., Lin, C., Feinstone, S. M., and Rice, C. M. (1993), "Expression and identification of hepatitis C virus polyprotein cleavage products", *J. Virol.* 67:1385–95.

Hijikata, M., Mizushima, H., Akagi, T., Mori, S., Kakiuchi, N., Kato, N., Tanaka, T., Kimura, K., and Shimotohno, K. (1993), "Two distinct proteinase activities required for the processing of a putative nonstructural precursor protein of hepatitis C virus", *J. Virol.* 67:4665–75.

Hijikata, M., Mizushima, H., Tanji, Y., Komoda, Y., Hirowatari, Y., Akagi, T., Kato, N., Kimura, K., and Shimotohno, K. (1993), "Proteolytic processing and membrane association of putative nonstructural proteins of hepatitis C virus", *Proc. Natl. Acad. Sci. USA* 90:10773–7.

Hong, Z., Ferrari, E., Wright-Minogue, J., Chase, R., Risano, C., Seeling, G., Lee, C.-G., and Kwong, A. (1996), "Enzymatic Characterization of Hepatitis C Virus NS3/4A Complexes Expressed in Mammalian Cells by Using the Herpes Simplex Virus Amplicon System", *J. Virol.* 70:4261–68.

Houghton, M. (1996). Hepatitis C virus, Fields, ed.

Jacob, J. R., Burk, K. H., Eichberg, J. W., Dreesman, G. R., and Lanford, R. E. (1990), "Expression of infectious viral particles by primary chimpanzee hepatocytes isolated during the acute phase of non-A, non-B hepatitis", *J. Infect. Dis.* 161:1121–7.

Kim, J. L., Morgenstern, K. A., Lin, C., Fox, T., Dwyer, M. D., Landro, J. A., Chambers, S. P., Markland, W., Lepre, C. A., O'Malley, E. T., Harbeson, S. L., Rice, C. M., Murcko, M. A., Caron, P. R., and Thomson, J. A. (1996), "Crystal structure of the hepatitis C virus NS3 protease domain complexed with a synthetic NS4A cofactor peptide", Cell 87:343–55.

Lo, S.-Y., Selby, M., and OU, J.-H. (1996), "Interaction between Hepatitis C Virus Core Protein and E1 Envelope Protein", *J. Virol.* 70: 5177–82.

Love, R. A., Parge, H. E., Wickersham, J. A., Hostomsky, Z., Habuka, N., Moomaw, E. W., Adachi, T., and Hostomska, Z. (1996), "The crystal structure of hepatitis C virus NS3 proteinase reveals a trypsin-like fold and a structural zinc binding site", Cell 87:331–42.

Miller, R. H., and Purcell, R. H. (1990), "Hepatitis C virus shares amino acid sequence similarity with pestiviruses and flaviviruses as well as members of two plant virus supergroups", *Proc. Natl. Acad. Sci. USA* 87:2057–61.

Nishiguchi, S., Kuroki, T., Nakatani, S., Morimoto, H., Takeda, T., Nakajima, S., Shiomi, S., Seki, S., Kobayashi, K., and Otani, S. (1995), "Randomized trial of effects of interferon-alpha on incidence of hepatocellular carcinoma in chronic active hepatitis C with cirrhosis", *Lancet* 346:1051–5.

Ohba, K., Mizokami, M., Lau, J. Y., Orito, E., Ikeo, K., and Gojobori, T. (1996), "Evolutionary relationship of hepatitis C, pesti-, flavi-, plantviruses, and newly discovered GB hepatitis agents", *FEBS Lett* 378:232–4.

Ray, R. B., Lagging, L. M., Meyer, K., and Ray, R. (1996), "Hepatitis C virus core protein cooperates with ras and transforms primary rat embryo fibroblasts to tumorigenic phenotype", *J. Virol.* 70:4438–43.

Sakamuro, D., Furukawa, T., and Takegami, T. (1995), "Hepatitis C virus nonstructural protein NS3 transforms NIH 3T3 cells", *J. Virol.* 69:3893–6.

Shimizu, Y. K., Hijikata, M., Iwamoto, A., Alter, H. J., Purcell, R. H., and Yoshikura, H. (1994), "Neutralizing antibodies against hepatitis C virus and the emergence of neutralization escape mutant viruses", *J. Virol.* 68:1494–500.

Shimizu, Y. K., Iwamoto, A., Hijikata, M., Purcell, R. H., and Yoshikura, H. (1992), "Evidence for in vitro replication of hepatitis C virus genome in a human T-cell line", *Proc. Natl. Acad. Sci. USA* 89:5477–81.

Suzich, J. A., Tamura, J. K., Palmer-Hill, F., Warrener, P., Grakoui, A., Rice, C. M., Feinstone, S. M., and Collett, M. S. (1993), "Hepatitis C virus NS3 protein polynucleotide-stimulated nucleoside triphosphatase and comparison with the related pestivirus and flavivirus enzymes", *J. Virol.* 67:6152–8.

Tanji, Y., Kaneko, T., Satoh, S., and Shimotohno, K. (1995), "Phosphorylation of hepatitis C virus-encoded nonstructural protein NS5A", *J. Virol.* 69:3980–3986.

---

What is claimed is:

1. A purified nucleic acid molecule comprising the DNA sequence of SEQ ID NO:2.

2. A purified nucleic acid molecule encoding an amino acid sequence comprising the sequence of SEQ ID NO:1.

3. A purified nucleic acid molecule degenerate from SEQ ID NO: 2 as a result of the genetic code, wherein the purified nucleic acid molecule encodes the amino acid sequence of SEQ ID NO: 1.

4. A recombinant vector that directs the expression of a nucleic acid molecule selected from the group consisting of the purified nucleic acid molecules of claim 1, 2, or 3.

5. A host cell transfected or transduced with the vector of claim 4.

6. A method for the production of core+1 polypeptide comprising culturing a host cell of claim 5 under conditions promoting expression, and recovering the polypeptide from the culture medium.

7. The method of claim 6, wherein the host cell is selected from the group consisting of bacterial cells, yeast cells, plant cells, and animal cells.

8. A method for the production of core+1 polypeptide comprising culturing a host cell transfected or transduced with a recombinant vector as claimed in claim 4 under conditions promoting expression, and recovering the polypeptide from the culture medium.

9. The method of claim 8, wherein the host cell is selected from the group consisting of bacterial cells, yeast cells, plant cells, and animal cells.

10. A host cell transfected or transduced with the recombinant vector as claimed in claim 4.

11. A method for the production of core+1 polypeptide comprising culturing a host cell of claim 10 under conditions promoting expression, and recovering the polypeptide from the culture medium.

12. The method of claim 11, wherein the host cell is selected from the group consisting of bacterial cells, yeast cells, plant cells, and animal cells.

13. A plasmid selected from the group consisting of pHPI 643, pHPI 644, pHPI 663, and pHPI 668.

* * * * *

UNITED STATES PATENT AND TRADEMARK OFFICE
CERTIFICATE OF CORRECTION

PATENT NO.     : 6,803,214 B1
DATED          : October 12, 2003
INVENTOR(S)    : Penelope Mavromara, Agoritsa Varaklioto and Urania Georgopoulou It is certified that error appears in the above-identified patent and that said Letters Patent is hereby corrected as shown below:

Column 31,
Line 12, "claim 1, 2, or 3." should read -- claims 1, 2, and 3. --.

Column 32,
Line 18, after "consisting of" insert -- pHPI 600, --.

Signed and Sealed this

Fourteenth Day of December, 2004

JON W. DUDAS
*Director of the United States Patent and Trademark Office*

SEQUENCE LISTING

```
<160> NUMBER OF SEQ ID NOS: 16

<210> SEQ ID NO 1
<211> LENGTH: 164
<212> TYPE: PRT
<213> ORGANISM: Hepatitis C virus

<400> SEQUENCE: 1

Ala Arg Ile Leu Asn Leu Lys Lys Thr Asn Val Thr Pro Thr Val
1               5                   10                  15

Ala His Arg Thr Ser Ser Ser Arg Val Ala Val Arg Ser Leu Val Glu
                20                  25                  30

Phe Thr Cys Cys Arg Ala Gly Ala Leu Asp Trp Val Cys Ala Arg Arg
            35                  40                  45

Glu Arg Leu Pro Ser Gly Arg Asn Leu Glu Val Asp Val Ser Leu Ser
    50                  55                  60

Pro Arg Leu Val Gly Pro Arg Ala Gly Pro Gly Leu Ser Pro Gly Thr
65                  70                  75                  80

Leu Gly Pro Ser Met Ala Met Arg Ala Ala Gly Gly Arg Asp Gly Ser
                85                  90                  95

Cys Leu Pro Val Ala Leu Gly Leu Ala Gly Ala Pro Gln Thr Pro Gly
            100                 105                 110

Val Gly Arg Ala Ile Trp Val Arg Ser Ser Ile Pro Leu Arg Ala Ala
        115                 120                 125

Ser Pro Thr Ser Trp Gly Thr Tyr Arg Ser Ser Ala Pro Leu Leu Glu
    130                 135                 140

Ala Leu Pro Gly Pro Trp Arg Met Ala Ser Gly Phe Trp Lys Thr Ala
145                 150                 155                 160

Thr Met Gln Gln

<210> SEQ ID NO 2
<211> LENGTH: 499
<212> TYPE: DNA
```

```
<213> ORGANISM: Hepatitis C virus
<220> FEATURE:
<221> NAME/KEY: CDS
<222> LOCATION: (5)..(484)
<221> NAME/KEY: CDS
<222> LOCATION: (488)..(499)

<400> SEQUENCE: 2 atga gca cga atc cta aac ctc aaa aaa aaa aca aac gta aca cca acc      49
     Ala Arg Ile Leu Asn Leu Lys Lys Lys Thr Asn Val Thr Pro Thr
      1               5                  10                  15 gtc gcc cac agg acg tca agt tcc cgg gtg gcg gtc aga tcg ttg gtg      97
Val Ala His Arg Thr Ser Ser Ser Arg Val Ala Val Arg Ser Leu Val
                 20                  25                  30 gag ttt act tgt tgc cgc gca ggg gcc cta gat tgg gtg tgc gcg cga     145
Glu Phe Thr Cys Cys Arg Ala Gly Ala Leu Asp Trp Val Cys Ala Arg
             35                  40                  45 cga gaa aga ctt ccg agc ggt cgc aac ctc gag gta gac gtc agc cta     193
Arg Glu Arg Leu Pro Ser Gly Arg Asn Leu Glu Val Asp Val Ser Leu
         50                  55                  60 tcc cca agg ctc gtc ggc ccg agg gca gga cct ggg ctc agc ccg ggt     241
Ser Pro Arg Leu Val Gly Pro Arg Ala Gly Pro Gly Leu Ser Pro Gly
 65                  70                  75 acc ctt ggc ccc tct atg gca atg agg gct gcg ggt ggg cgg gat ggc     289
Thr Leu Gly Pro Ser Met Ala Met Arg Ala Ala Gly Gly Arg Asp Gly
 80                  85                  90                  95 tcc tgt ctc ccc gtg gct ctc ggc cta gct ggg gcc cca cag acc ccc     337
Ser Cys Leu Pro Val Ala Leu Gly Leu Ala Gly Ala Pro Gln Thr Pro
                100                 105                 110 ggc gta ggt cgc gca att tgg gta agg tca tcg ata ccc tta cgt gcg     385
Gly Val Gly Arg Ala Ile Trp Val Arg Ser Ser Ile Pro Leu Arg Ala
            115                 120                 125 gct tcg ccg acc tca tgg ggt aca tac cgc tcg tcg gcg ccc ctc ttg     433
Ala Ser Pro Thr Ser Trp Gly Thr Tyr Arg Ser Ser Ala Pro Leu Leu
        130                 135                 140 gag gcg ctg cca ggg ccc tgg cgc atg gcg tcc ggg ttc tgg aag acg     481
Glu Ala Leu Pro Gly Pro Trp Arg Met Ala Ser Gly Phe Trp Lys Thr
    145                 150                 155 gcg tga act atg caa cag                                             499
Ala     Thr Met Gln Gln
160

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (16)..(39)

<400> SEQUENCE: 3
tcagaattcg gatca atc cta aac ctc aaa aaa aaa aca                     39
               Ile Leu Asn Leu Lys Lys Lys Thr
                1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Ile Leu Asn Leu Lys Lys Lys Thr
 1               5

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (13)..(33)

<400> SEQUENCE: 5
atcgagggaa gg gtc gcc cac agg acg tca agt                        33
              Val Ala His Arg Thr Ser Ser
                1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ala His Arg Thr Ser Ser
 1               5

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (22)..(45)

<400> SEQUENCE: 7
atccccggga attcgaagct a atc cta aac ctc aaa aaa aaa aca          45
                       Ile Leu Asn Leu Lys Lys Lys Thr
                        1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Leu Asn Leu Lys Lys Lys Thr
 1               5

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (19)..(39)

<400> SEQUENCE: 9
```

```
gggatccccg ggaattcc gta aca cca acc gtc gcc cac            39
                    Val Thr Pro Thr Val Ala His
                     1               5
```

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Thr Pro Thr Val Ala His
 1               5

<210> SEQ ID NO 11
<211> LENGTH: 480
<212> TYPE: RNA
<213> ORGANISM: Hepatitis C virus

<400> SEQUENCE: 11

```
augagcacga auccuaaacc ucaaaaaaaa aacaaacgua acaccaaccg ucgcccacag     60
gacgucaagu ucccgggugg cggucagauc guuggnggag uuuacuuguu gccgcgcagg    120
ggcccuagau uggguguscg cgcgacgaga aagacuuccg agcggucgca accucgaggu    180
agacgucagc cuaucccaa ggcucgucgg cccgagggca ggaccugggc ucagcccggg     240
uacccuuggc cccucuaugg caaugagggc ugcggguggg cgggauggcu ccugucuccc    300
cguggcucuc ggccuagcug gggccccaca gaccccggc guaggucgcg caauuugggu     360
aaggucaucg auaccuuac gucggcuuc gccgaccuca uggggauacau accgcucguc    420 ggcgccccuc uuggaggcgc ugccagggcc cuggcgcaug gcuccgggu ucuggaagac     480
```

<210> SEQ ID NO 12
<211> LENGTH: 480
<212> TYPE: RNA
<213> ORGANISM: Hepatitis C virus

<400> SEQUENCE: 12

```
augagcacga auccuaaacc ucaaaaaaaa aacaaacgua acaccaaccg ucgcccucag     60
gacgucaagu ucccgggugg cggucagauc guuggnggag uuuacuuguu gccgcgcagg    120
ggcccuagau uggguguscg cgcgacgaga aagacuuccg agcggucgca accucgaggu    180
agacgucagc cuaucccaa ggcucgucgg cccgagggca ggaccugggc ucagcccggg     240
uacccuuggc cccucuaugg caaugagggc ugcggguggg cgggauggcu ccugucuccc    300
cguggcucuc ggccuagcug gggccccaca gaccccggc guaggucgcg caauuugggu     360
aaggucaucg auaccuuac gucggcuuc gccgaccuca uggguacau accgcucguc      420 ggcgccccuc uuggaggcgc ugccagggcc cuggcgcaug gcguccgggu ucuggaagac    480
```

<210> SEQ ID NO 13
<211> LENGTH: 480
<212> TYPE: RNA
<213> ORGANISM: Hepatitis C virus

<400> SEQUENCE: 13

```
augagcacga auccuaaacc ucaaaaaaaa aacaaacgua acaccaaccg ucgcccacag     60
gacgucaagu ucccgggugg cggucagauc guuggnggag uuuacuugcu cccgcgcagg    120
```

| | | | | |
|---|---|---|---|---|
| ggcccuagau | uggguguglcg | cgcgacgaga | aagacuuccg | agcggucgca | accucgaggu | 180 |
| agacgucagc | cuaucccaa | ggcucgucgg | cccgagggca | ggaccugggc | ucagcccggg | 240 |
| uacccuugge | cccucuaugg | caaugagggc | ugcgggugg | cgggauggcu | ccugucuccc | 300 |
| cguggcucuc | ggccuagcug | ggccccaca | gaccccggc | guaggucgcg | caauuugggu | 360 |
| aaggucaucg | auacccuuac | gugcggcuuc | gccgaccuca | uggguacau | accgcucguc | 420 |
| ggcgccccuc | uuggaggcgc | ugccagggcc | cuggcgcaug | gcguccgggu | ucuggaagac | 480 |

<210> SEQ ID NO 14
<211> LENGTH: 480
<212> TYPE: RNA
<213> ORGANISM: Hepatitis C virus

<400> SEQUENCE: 14

| | | | | | | |
|---|---|---|---|---|---|---|
| augagcacga | auccuaaacc | ucaaaaaaaa | aacaaacgua | acaccaaccg | ucgcccucag | 60 |
| gacgucaagu | ucccgggugg | cggucagauc | guugguggag | uuuacuugcu | cccgcgcagg | 120 |
| ggcccuagau | uggguguglcg | cgcgacgaga | aagacuuccg | agcggucgca | accucgaggu | 180 |
| agacgucagc | cuauccccaa | ggcucgucgg | cccgagggca | ggaccugggc | ucagcccggg | 240 |
| uacccuugge | cccucuaugg | caaugagggc | ugcgggugg | cgggauggcu | ccugucuccc | 300 |
| cguggcucuc | ggccuagcug | ggccccaca | gaccccggc | guaggucgcg | caauuugggu | 360 |
| aaggucaucg | auacccuuac | gugcggcuuc | gccgaccuca | uggguacau | accgcucguc | 420 |
| ggcgccccuc | uuggaggcgc | ugccagggcc | cuggcgcaug | gcguccgggu | ucuggaagac | 480 |

<210> SEQ ID NO 15
<211> LENGTH: 480
<212> TYPE: RNA
<213> ORGANISM: Hepatitis C virus

<400> SEQUENCE: 15

| | | | | | | |
|---|---|---|---|---|---|---|
| augagcacga | auccuaaacc | ucaaaaaaaa | aacaaacgua | acaccaaccg | ucgcccacag | 60 |
| gacgucaagu | ucccgggugg | cggucagauc | guugguggag | uuuacuggug | gccgcgcagg | 120 |
| ggcccuagau | uggguguglcg | cgcgacgaga | aagacuuccg | agcggucgca | accucgaggu | 180 |
| agacgucagc | cuauccccaa | ggcucgucgg | cccgagggca | ggaccugggc | ucagcccggg | 240 |
| uacccuugge | cccucuaugg | caaugagggc | ugcgggugg | cgggauggcu | ccugucuccc | 300 |
| cguggcucuc | ggccuagcug | ggccccaca | gaccccggc | guaggucgcg | caauuugggu | 360 |
| aaggucaucg | auacccuuac | gugcggcuuc | gccgaccuca | uggguacau | accgcucguc | 420 |
| ggcgccccuc | uuggaggcgc | ugccagggcc | cuggcgcaug | gcguccgggu | ucuggaagac | 480 |

<210> SEQ ID NO 16
<211> LENGTH: 480
<212> TYPE: RNA
<213> ORGANISM: Hepatitis C virus

<400> SEQUENCE: 16

| | | | | | | |
|---|---|---|---|---|---|---|
| augagcacga | auccuaaacc | ucaaaaaaaa | aacaaacgua | acaccaaccg | ucgcccacag | 60 |
| gacgucaagu | ucccgggugg | cggucagauc | guugguggag | uuuacuugau | gccgcgcagg | 120 |
| ggcccuagau | uggguguglcg | cgcgacgaga | aagacuuccg | agcggucgca | accucgaggu | 180 |
| agacgucagc | cuauccccaa | ggcucgucgg | cccgagggca | ggaccugggc | ucagcccggg | 240 |
| uacccuugge | cccucuaugg | caaugagggc | ugcgggugg | cgggauggcu | ccugucuccc | 300 |
| cguggcucuc | ggccuagcug | ggccccaca | gaccccggc | guaggucgcg | caauuugggu | 360 |
| aaggucaucg | auacccuuac | gugcggcuuc | gccgaccuca | uggguacau | accgcucguc | 420 |
| ggcgccccuc | uuggaggcgc | ugccagggcc | cuggcgcaug | gcguccgggu | ucuggaagac | 480 |